US010940175B2

(12) United States Patent
Blain et al.

(10) Patent No.: US 10,940,175 B2
(45) Date of Patent: Mar. 9, 2021

(54) INHIBITOR OF INFLAMMATORY CONDITIONS

(71) Applicant: Compton Developments Ltd., Swansea (GB)

(72) Inventors: Emma Jane Blain, Cardiff (GB); Victor Collin Duance, Cardiff (GB); Ahmed Yasine Ali, Swansea (GB); Ifor Delme Bowen, Cardiff (GB)

(73) Assignee: COMPTON DEVELOPMENTS LTD., Swansea (GB)

( * ) Notice: Subject to any disclaimer, the term of this patent is extended or adjusted under 35 U.S.C. 154(b) by 590 days.

(21) Appl. No.: 15/227,054

(22) Filed: Aug. 3, 2016

(65) Prior Publication Data

US 2017/0049833 A1 Feb. 23, 2017

Related U.S. Application Data

(63) Continuation-in-part of application No. 13/384,645, filed as application No. PCT/GB2010/001286 on Jul. 5, 2010, now Pat. No. 9,439,936.

(30) Foreign Application Priority Data

Jul. 18, 2009 (GB) ...................................... 0912526
Dec. 2, 2009 (GB) ...................................... 0921086

(51) Int. Cl.
*A61K 36/324* (2006.01)
*A61K 31/56* (2006.01)

(52) U.S. Cl.
CPC ............ *A61K 36/324* (2013.01); *A61K 31/56* (2013.01); *A61K 2236/33* (2013.01)

(58) Field of Classification Search
CPC ... A61K 36/324; A61K 31/56; A61K 2236/33
See application file for complete search history.

(56) References Cited

U.S. PATENT DOCUMENTS

| 5,720,975 | A | 2/1998 | Etzel | |
|---|---|---|---|---|
| 2006/0177467 | A1 | 8/2006 | Striggow et al. | |
| 2008/0275117 | A1* | 11/2008 | Li | A61K 31/19 514/546 |

OTHER PUBLICATIONS

Frank et al. J. Chromatogr. A 1112 (2006) 255-262 (Year: 2006).*
Bennett et al. "Methanol" from Clinical Pharmacology E-Book: With Studentconsult Access. p. 137. (Year: 2008).*
Morgan, E.T. Clin Pharmacol Ther. April ; 85(4): 434-438 (pp. 1-10). (Year: 2009).*
"CDC: Sepsis". Web Publication Date: Jun. 27, 2018. Retrieved from the Internet on: Feb. 22, 2020. Retrieved from: <URL: https://www.cdc.gov/sepsis/diagnosis/index.html>.1 page. (Year: 2018).*
NIH: National Institute of Aging. Treatment of Alzheimer's Disease. Web Publication date: Jan. 4, 2018. Retrieved from the Internet on: Feb. 22, 2020. Retrieved from: <URL: https://www.nia.nih.gov/health/how-alzheimers-disease-treated>. 16 pages. (Year: 2018).*
Mayo Clinic: Asthma. Retrieved from the internet on: Feb. 22, 2020. Retrieved from: <URL: https://www.mayoclinic.org/diseases-conditions/asthma/diagnosis-treatment/drc-20369660?p=1>. 10 pages, (Year: 2020).*
MedlinePlus: Duchenne muscular dystrophy. Web Publication Date: Feb. 18, 2020. Retrieved from the Internet on: Feb. 22, 2020. Retrieved from: <URL: https://medlineplus.gov/ency/article/000705.htm>. 6 pages. (Year: 2020).*
Pranav K. Chaturvedi, et al.; "Lupeol: Connotations for chemoprevention"; Elsevier, Cancer Letters vol. 263 (2008) pp. 1-13; Proteomics Labratory, India.
G. Strappaghetti, et al.; "Constituents of Essential Oil of Boswella Frereana"; Phytochemistry, vol. 21, No. 8, pp. 2114-2115 (1982); Pergamon Press Ltd., GB.
Simla Basar, Comparative Studies on the Essential Oils, Pyrolysates and Boswellic Acids; Dissertation for the fulfillment of the requirements for the degree of Dr. rer. nat.; Retrieved from the internet on Oct. 21, 2010 URL: http://www.chemie.uni-hamburg.de/bibliothek/2005/DissertationBasar.pdf; Consists of front pages, acknowledgements, Contents, pp. 1-231, list of abbreviations, list of chemicals, and curriculum vitae.
T. Geetha, et al.; "Effect of lupeol and lupeol linoleate on lysosomal enzymes and collagen in adjuvant-induced arthritis in rats"; Molecular and Cellular Biochemistry vol. 201; pp. 83-87; Kluwer Academic Publishers 1999, Netherlands.
"Boswellia serrata"; Alternative Medicine Review, vol. 13, No. 2 (Jun. 2008), pp. 165-167; Thorne Research, Inc. 2008.
Maria Angeles Fernandez, et al.; "New insights into the mechanism of action of the anti-inflammatory triterpene lupeol"; Journal of Pharmacy and Pharmacology, vol. 53, No. 11, (Nov. 1, 2001) pp. 1533-1539.
Emma J. Blain, et al.; "*Boswellia frereana* (Frankincense) Suppresses Cyokine-Induced Matrix Metalloproteinase Expression and Production of Pro-Inflammatory Molecules in Articular Cartilage"; Phytotherapy Research, vol. 24, pp. 905-912 (2010); Published in Wiley InterScience, Nov. 26, 2009.
Michaela Mertens, et al.; "The volatile constituents of frankincense—a review"; Flavour and Fragrance Journal, vol. 24, pp. 279-300; Published in Wiley InterScience, Aug. 10, 2009.
University of Rochester Medical Center. "How to Prevent Osteoarthritis". Retrieved from the Internet on: Mar. 1, 2015. Retrieved from the Internet< URL: http://www.urmc.rochester.edu/encyciopedia/content.aspx?ContentTypeI0=1&ContentI 0=1411 >.

(Continued)

*Primary Examiner* — Amy L Clark
(74) *Attorney, Agent, or Firm* — King & Schickli, PLLC

(57) ABSTRACT

The invention relates to *Boswellia frereana* and particularly an extract of same for treating a range of inflammatory disorder or conditions selected from the group comprising: inflammatory bowel disease (IBD), all forms of muscular dystrophy especially Duchenne muscular dystrophy, sepsis, sepsis syndrome, osteoporosis, ischemic injury, graft vs. host disease, reperfusion injury, asthma, diabetes, cancer, myelogenous and other leukemias, psoriasis and cachexia, Alzheimer's Disease, demyelinating neurological disorders including multiple sclerosis, acetylcholinesterase mediated disorders, retinal disorders, neurological, retinal, and muscular disorders.

10 Claims, 28 Drawing Sheets
Specification includes a Sequence Listing.

(56) References Cited

OTHER PUBLICATIONS

Quest Int UK Ltd. Use of Boswellia extracts, menthyl pyrrolidone carboxylate, ceramides and pongamol are useful in e.g. cosmetics, food stuffs and pharmaceuticals. RO 422034 A. Jun. 10, 1999. Abstract only.
Olibanum from "Remington and Wood, 1918: the US dispensatory". Retrieved from the Internet: "Henriette's Herbal Homepage" on Jul. 8, 2013. Retrieved from: <URL:http://www.henriettesherbal.com/eclectic/usdisp/boswellia.html>.
Mathe et al. "High-Performance Liquid Chromatographic Analysis of Triterpenoids in Commercial Frankincense". Chromatographia, vol. 60 (2004) pp. 493-499.
A. Frank, et al. "Analysis of frankincense from various *Boswellia* species with inhibitory activity on human drug metabolising cytochrome P450 enzymes using liquid chromatography mass spectrometry after automated on-line extraction." J. Chromatography A, 1112 (2006) 255-262. Elsevier, www.sciencedirect.com.

\* cited by examiner

A.

B.

A.

pro-MMP9 →
pro-MMP2 →
active MMP2 →

| | | | | |
|---|---|---|---|---|
| 5ng/ml IL-1α & 10ng/ml OSM | - | + | - | + |
| 100µg/ml B. frereana | - | - | + | + |

| | | | | |
|---|---|---|---|---|
| Pro-MMP9 | 0.06 ± 0.02 | 0.59 ± 0.03*** | 0 | 0.09 ± 0.01*** |
| Pro-MMP2 | 0.67 ± 0.03 | 0.76 ± 0.06 | 0.68 ± 0.02 | 0.60 ± 0.05 |
| Active MMP2 | 0.17 ± 0.05 | 0.11 ± 0.02 | 0.21 ± 0.02 | 0.10 ± 0.01 |

B.

pro-MMP9 →
active MMP9 →
pro-MMP2 →
active MMP2 →

| | | | | |
|---|---|---|---|---|
| 5ng/ml IL-1α & 10ng/ml OSM | - | + | - | + |
| 100µg/ml B. frereana | - | - | + | + |

| | | | | |
|---|---|---|---|---|
| Pro-MMP9 | 0 | 0.58 ± 0.04 | 0 | 0 |
| Active MMP9 | 0 | 0.98 ± 0.28 | 0 | 0 |
| Pro-MMP2 | 0.49 ± 0.02 | 0.58 ± 0.09 | 0.54 ± 0.13 | 0.27 ± 0.04 |
| Active MMP2 | 0.21 ± 0.04 | 0.38 ± 0.15 | 0.14 ± 0.05 | 0.06 ± 0.01* |

C.

| mRNA expression | untreated | 5ng/ml IL-1α + 10ng/ml OSM | 100µg/ml B. frereana | 5ng/ml IL-1α + 10ng/ml OSM + 100µg/ml B. frereana |
|---|---|---|---|---|
| MMP 9 | N.D. | 1.05 ± 0.18 | N.D. | 0.58 ± 0.13 |

| I.D. | Compound | % Peak Area |
| --- | --- | --- |
| 1 | α-Thujene | 0.34 |
| 2 | α-Phellandrene | 0.074 |
|  | m-Cymene | trace |
| 3 | p-Cymene | 0.136 |
| 4 | Thujol | 0.135 |
| 5 | Eucalyptol | 0.058 |
| 6 | Thujol | 0.042 |
| 7 | Unknown | 0.05 |
| 8 | Thujone | 0.05 |
|  | Sabinol | trace |
| 9 | Unknown | 0.047 |
| 10 | Unknown | 0135 |
| 11 | β-Bourbonene | 0.095 |
|  | t-Cadinol | trace |
|  | Phellandrene dimer 1 | trace |
|  | Phellandrene dimer 2 | trace |
| 12 | Phellandrene dimer 3 | 1.103 |
| 13 | Phellandrene dimer 4 | 0.042 |
| 14 | Phellandrene dimer 5 | 0.243 |
| 15 | Lupeol | 0.087 |
| 16 | β-Amyrin | 6.357 |
| 17 | α-Amyrin | 2.384 |
| 18 | epi-Lupeol | 59.328 |
| 19 | Lupeol analogue | 7.266 |
| 20 | Lupeol acetate | 3.105 |
| 21 | Unknown | 2.093 |
| 22 | Unknown | 6.676 |
|  | % Compounds identified | 80.85 |

Figure 6 (cont)

epi-Lupeol

β-Amyrin

α-Phellandrene dimer

Group 1 = Naïve Control    Group 2 = Vehicle Control
Group 3 = Bos Ext 25mg/kg   Group 4 = Bos Ext 50mg/kg
Group 5 = Bos Ext 100mg/kg  Group 6 = Bos Ext 200mg/kg INH-01: DSS-Induced Colitis Endoscopy Images Day 7

Group 1 = Naïve Control
Group 2 = Vehicle Control
Group 3 = Bos Ext 25mg/kg
Group 4 = Bos Ext 50mg/kg
Group 5 = Bos Ext 100mg/kg
Group 6 = Bos Ext 200mg/kg

INHIBITOR OF INFLAMMATORY CONDITIONS

This application is a continuation-in-part of U.S. patent application Ser. No. 13/384,645 filed on Feb. 28, 2012 which claims priority from PCT patent application PCT/GB2010/001286 filed on Jul. 5, 2010 which in turn claims priority from British Patent Application No. GB 0921086.5 filed on Dec. 2, 2009 and British Patent Application No. GB 0912526.1 filed on Jul. 18, 2009, the disclosures of which are incorporated herein by reference in their entirety.

REFERENCE TO SEQUENCE LISTING SUBMITTED ELECTRONICALLY

A sequence listing electronically submitted with the present application as an ASCII text file named 1776-004CIP_ST25.txt, created on Jul. 29, 2016 and having a size of 1679 bytes, is incorporated herein by reference in its entirety.

TECHNICAL FIELD

The invention relates to the use of *Boswellia frereana* (commonly known as frankincense) as a medicament; an extract of *Boswellia frereana* wherein the extract is soluble in an organic solvent and does not comprise boswellic acid; at least one agent of said extract; and a composition derived from *Boswellia frereana*. The invention further relates to a method for obtaining and therapeutically using said extract, and/or said agent and/or said composition and, particularly, but not exclusively, using said extract, and/or said agent and/or composition as an inhibitor of an inflammatory condition such as, for example, inflammatory bowel disease (IBD).

*Boswellia frereana* is a natural product of Somalia, Africa. The product can be sourced from a number of suppliers including International Gums & Oils Limited [The Maltings, East Tyndall Street, Cardiff, CF24 5EA]; Simply Incense [Resolve (WSS Ltd t/a), Unit 12, Southwell Business Centre, Crew Lane Industrial Estate, Southwell, Nottinghamshire, NG25 0TX]; A F Suter & Co. ltd. [Unit 1, Beckingham Business Park, Beckingham Road, Tolleshunt Major, Essex, United Kingdom]; and Joseph Flach & Sons Ltd. [Unit 8, Maxwell Road, Woodston Industrial Estate, Peterborough, Cambridgeshire, PE2 7HU, ENGLAND]

BACKGROUND

Articular cartilage degradation is a classical feature of both degenerative and inflammatory arthritides e.g. osteoarthritis (OA) and rheumatoid arthritis (RA). OA is characterised by a loss of the proteoglycans and collagen in the extracellular matrix (ECM), and these catabolic events are primarily mediated by the matrix metalloproteinases (MMPs) 1, 3, 9, and 13 (1-6)) and aggrecanases (ADAMTS-4 and -5 (6-8)). The differential expression of these catabolic enzymes is related to the level of inflammatory mediators and cytokines in the OA joint. Cytokines such as interleukin-1 (IL-1) and tumour necrosis factor-α (TNF-α) are key mediators in driving ECM destruction. In addition to inducing the synthesis of MMPs and aggrecanases, IL-1 and TNF-α also stimulate production of nitric oxide, via inducible nitric oxide synthase, and increase the synthesis of prostaglandin E2 (PGE2), by stimulating the expression of PGE2 synthase and cyclo-oxygenase 2 (COX-2).

The incidence of OA is prevalent in an ageing or obese population; there are estimates of 100 million people with OA in the European Union (9), and in the United States, the burden of clinical OA has risen to nearly 27 million people in 2007 (10). Relieving pain and stiffness, improving physical function and delaying disease progression are important therapeutic goals for managing OA. Non-opioid analgesics, non-steroidal anti-inflammatory drugs (NSAIDs) and intra-articular therapies are currently prescribed; continued use of NSAIDs has been associated with G.I. tract bleeding, and an increased risk of other adverse side effects (11), making them far from ideal for treating a chronic pathology. Therefore, identifying other potential pharmaceutical agents which may be used to alleviate the symptoms associated with OA, whilst remaining efficacious and non-toxic, is an ongoing pursuit.

The most common forms of inflammatory bowel disease (IBD), Crohn's disease and ulcerative colitis, are chronic and progressive inflammatory disorders of the digestive tract. Crohn's disease usually affects both ileum and colon while ulcerative colitis usually affects only the innermost lining of the colon and rectum. The symptoms for Crohn's disease and ulcerative colitis are generally similar with abdominal pain and Diarrhoea. In moderate to severe ulcerative colitis, bloody stool is often observed. There is currently no cure for IBD. Drugs and biologics are commonly used to treat symptoms, induce remission and prevent relapse. Anti-inflammatory drugs such as sulfasalazine, mesalamine and corticosteroids are often the first line medications for the treatment of IBD to induce remission, while immune system suppressors are generally used to help maintain remission. The most common immune system modulators used for treating IBD are azathioprine, mercaptopurine and biological therapies such as anti-tumor necrosis factor (anti-TNF-α).

However, as will be apparent to those skilled in the art, the medicament described herein has application in the treatment of any inflammatory condition in which MMP9, PGE2 and NO are elevated or which are Interleukin-1 mediated such as rheumatoid arthritis (RA), inflammatory bowel disease (IBD), sepsis, sepsis syndrome, osteoporosis, ischemic injury, graft vs. host disease, reperfusion injury, asthma, diabetes, myelogenous and other leukemias, psoriasis and cachexia, Alzheimer's Disease, demyelinating neurological disorders including multiple sclerosis, retinal disorders, neurological, retinal, and muscular disorders.

In recent years, there has been a growing interest in the use of compounds derived from herbs in alleviating the symptoms of a variety of diseases such as OA, breast and prostate cancer, neuronal plasticity/memory loss, encephalomyelitis and inflammatory bowel disease.

Preparations from the oleo resin of the *Boswellia* genus (other than *B. frereana*), commonly known as frankincense, have been identified as potent anti-inflammatory, anti-arthritic and anti-analgesic agents (recently reviewed in (15, 16)). Traditionally, *Boswellia serrata* species has been used extensively in treating conditions which are either initiated by or maintained by inflammatory events, including collagenous colitis (17), Crohn's disease (18), and both rheumatoid (19, 20) and osteoarthritis (21-23). The studies demonstrated that *B. serrata* had some efficacy in treating these inflammatory conditions. In two different animal models of arthritis (carrageenan-induced and antigen-induced), topical administration of *B. serrata* to the site of inflammation reduced rat paw edema by approximately 50% (20). The main pharmacologically active ingredients of *B. serrata* are α- and β-boswellic acids (24), and Singh et al intimated that the α- or β-boswellic acid was able to act in both early and late phases of inflammation (20). *B. serrata* is believed to exert its anti-inflammatory properties by inhibiting 5-lipoxygenase in a selective, enzyme-linked non-redox and non-competitive manner (25), and by inhibiting COX-1 activity (26).

Recently, the efficacy of 5-Loxin®, a novel *B. serrata* extract enriched with 30% 3-O-acetyl-11-keto-β-boswellic acid, has been tested in human clinical trials for the treatment of knee OA (23). Significant improvements in pain score and functional ability, and a reduction in synovial fluid MMP 3 were observed (23).

Apart from *B. serrata* (native to India), other members of the *Boswellia* family have also been identified including *B. sacra* (native to Arabian peninsula) and *B. carteri* (27) and frereana (native to Africa).

Our work has shown that *B. frereana* does not contain boswellic acid (alpha or beta), the main pharmacologically active ingredient of *B. Serrata*, it is therefore surprising to discover that *B. frereana* is effective as an anti-inflammatory and interesting to discover that this anti-inflammatory effect operates via a different pathway to that used by other members of the *Boswellian* genus. Indeed we have discovered that the pharmacologically active component(s) of *B. frereana* operates, at least partly, via the suppression, deactivation or inhibition of matrix metalloproteinase 9 (MMP9). Additionally, we have also discovered that *B. frereana* inhibits acetylcholinesterase activity and so this makes it useful for treating neurological disorders where inhibition of acetylcholinesterase is of benefit, such as Alzheimer's disease. Moreover, we have also shown that *B. frereana* is effective at killing cancer cells and so this makes it useful for treating cancer, in particular breast cancer.

SUMMARY

According to a first aspect, the invention concerns *Boswellia frereana* for use as a medicament. More ideally the invention concerns an extract of *Boswellia frereana*, more particularly an effective amount of an alcohol extract of *Boswellia frereana*, wherein said extract comprises epi-lupeol or a salt thereof, and wherein the extract is devoid of boswellic acids.

Preferably the medicament or extract is used to treat or prevent an inflammatory disorder such as, but not limited to, IBD. More preferably still, the medicament or extract is used to treat any one or more of the following conditions: inflammatory bowel disease (IBD), all forms of muscular dystrophy especially Duchenne muscular dystrophy, sepsis, sepsis syndrome, osteoporosis, ischemic injury, graft vs. host disease, reperfusion injury, asthma, diabetes, cancer, myelogenous and other leukemias, psoriasis and cachexia, Alzheimer's Disease, demyelinating neurological disorders including multiple sclerosis, Acetylcholinesterase mediated disorders, retinal disorders, neurological, retinal, and muscular disorders.

Ideally the individual suffering from the inflammatory disorder or said condition is a mammal and most preferably a primate or grazing animal such as a bovine, ovine, equine, or porcine, alternatively the individual is a feline, canine or rodent. Most preferably the individual is a human.

There is also provided the use of *Boswellia frereana* extract in the preparation of an agent for the treatment or prevention of the disorders or conditions set out above.

The invention also provides a method for the treatment or prevention of the disorders or conditions set out above, the method comprising administering to a patient in need of such treatment an effective amount of the extract of *Boswellia frereana*.

Ideally the patient is a mammal and most preferably a primate or grazing animal such as a bovine, ovine, equine, or porcine, alternatively the individual is a feline, canine or rodent. Most preferably the individual is a human.

According to a further aspect of the invention there is provided an extract of *Boswellia frereana* wherein said extract is soluble in organic solution and comprises one or more of:

a) an inhibitor of matrix metalloproteinase 9 (MMP9),
b) an inhibitor of NO synthesis,
c) an inhibitor of $PGE_2$ synthesis; and
d) said extract does not affect the 5-lipoxygenase pathway; and
e) said extract does not comprise alpha or beta boswellic acid.

In the context of the present invention the term "extract of *Boswellia frereana*" refers to a mixture of components which are present in the oleo-resin of *Boswellia frereana* and which are soluble in a suitable organic solvent. The extract may be obtained by mixing the gum resin with the solvent and leaving for a suitable period of time, for example several days, in a light-free environment so that the soluble components of the gum are extracted into the solvent. Removing any insoluble resin. The solvent may then be removed to leave the extract. For the avoidance of doubt, "extract" does not refer to a single component but to the mixture of components.

The solvent may be a polar solvent, typically an alcohol such as methanol or ethanol or a non-polar solvent such as hexane. *B. frereana* is unique in this sense, as in other boswellia species hexane extracts the essential oil fraction (volataile oil) only and, also, in other *Boswellia* species ethanol isolates the resin fraction only. However, with *B. frereana* both hexane (non-polar) and ethanol (polar) isolate the resin fraction containing 60% epilupeol.

However, the extraction may also be carried out using other extraction solvents such as ethyl acetate, diethyl ether, chloroform, methylene chloride, petroleum ether, acetone, pentane, or toluene. Other suitable solvents will be well known to those skilled in the art of plant component extraction.

Preferably said extract comprises the pentacyclic triterpene epi-lupeol or a derivative thereof or a salt of any one of these.

Epi-lupeol is a diastereisomer of the pentacyclic triterpene lupeol. Diastereomers are defined as stereoisomers that are not enantiomers (i.e non-superimposable mirror images of each other). Diastereomers, sometimes called diastereoisomers generally have different physical properties and different reactivity to their isomers.

Other components of the extract comprise β-amyrin, α-amyrin, α-phellandrene dimers, α-thujene and α-phellandrene and their isomers and, where appropriate, salts. More preferably still, the extract has a GC-MS chromatogram as shown in FIG. 6. More preferably the main components are epi-lupeol, β-amyrin and alpha-phellandrene dimer.

In a further aspect of the invention there is provided the extract or an agent selected from epi-lupeol, β-amyrin, α-amyrin, α-phellandrene dimers, α-thujene and α-phellandrene; the isomers of these agents other than lupeol; where appropriate, pharmaceutically or veterinarily acceptable salts; and mixtures thereof, for use in medicine, particularly in the treatment or prevention of the inflammatory diseases and conditions set out above.

Appropriate pharmaceutically or veterinarily acceptable salts include basic addition salts such as sodium, potassium, calcium, aluminium, zinc, magnesium and other metal salts as well as choline, diethanolamine, ethanolamine, ethyl diamine, megulmine and other well-known basic addition salts as summarised in Paulekuhn et al., (2007) *J. Med. Chem.* 50: 6665-6672 and/or known to those skilled in the art.

The invention also provides the use of the extract or an agent selected from epi-lupeol, β-amyrin, α-amyrin, α-phellandrene dimers, α-thujene and α-phellandrene; the isomers of these agents other than lupeol; where appropriate their salts; and mixtures thereof in the preparation of a medicament for the treatment or prevention of the disorders or conditions as set out above.

In yet another aspect of the invention, there is provided a composition comprising the extract of the invention together with a carrier.

Generally, the composition will be a pharmaceutical or veterinary composition and the carrier will be a pharmaceutically or veterinarily acceptable carrier.

In an alternative aspect, there is provided a pharmaceutical composition comprising an agent selected from epi-lupeol, β-amyrin, α-amyrin, α-phellandrene dimers, α-thujene and α-phellandrene; the isomers of these agents other than lupeol; where appropriate, pharmaceutically or veterinarily acceptable salts; and mixtures thereof; together with a pharmaceutically acceptable carrier.

Other active materials may also be present, as may be considered appropriate or advisable for the disease or condition being treated or prevented. For example, the composition may also contain an antibiotic or antibacterial agent.

The carrier, or, if more than one be present, each of the carriers, must be acceptable in the sense of being compatible with the other ingredients of the formulation and not deleterious to the recipient.

The formulations include those suitable for nasal, bronchial (inhaled), topical (including eye drops, buccal and sublingual), parenteral (including subcutaneous, intramuscular, intraperitoneal, intravenous intra-articular and intradermal) administration and may be prepared by any methods well known in the art of pharmacy.

Preferred compositions are formulated for intra-articular, intravenous, parenteral, oral, nasal, bronchial or topical administration.

The composition may be prepared by bringing into association the extract of the invention and the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing an extract of the invention in conjunction or association with a pharmaceutically or veterinarily acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compounds may be made up into a cream, ointment, jelly, solution or suspension etc. Cream or ointment formulations that may be used for the drug are conventional formulations well known in the art, for example, as described in standard text books of pharmaceutics such as the British Pharmacopoeia. Extracts of the invention may be used for the treatment of the respiratory tract by nasal, bronchial or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Parenteral formulations will generally be sterile.

The precise amount of a extract of the present invention which is therapeutically effective, and the route by which such compound is best administered, is readily determined by one of ordinary skill in the art by comparing the blood level of the agent to the concentration required to have a therapeutic effect. In a further aspect of the invention there is provided a method for the treatment or prevention of a disorder or condition as set out above, the method comprising administering to a patient in need of such treatment an effective amount of:

a. an extract of the invention; or
b. an agent selected from epi-lupeol, β-amyrin, α-amyrin, α-phellandrene dimers, α-thujene and α-phellandrene; the isomers of these agents other than lupeol; where appropriate, their salts; and mixtures thereof; or
c. a composition according to the invention.

According to a further aspect of the invention there is provided a method for obtaining an extract of *Boswellia frereana* comprising:

a) obtaining oleo-resin from *Boswellia frereana*;
b) exposing said resin to an organic liquid in a light-impermeable environment;
c) removing any insoluble resin; and
d) removing the solvent to produce *Boswellia frereana* extract.

Removal of the solvent in step (d) may be achieved by evaporation.

Alternatively, precipitation of a solid triterpene fraction may be obtained by the addition of water to the organic extraction mixture, ideally, this step is undertaken after removing the insoluble resin.

In a preferred method of the invention the resin is exposed to an alcoholic solvent such as methanol or ethanol, preferably ethanol, and ideally 100% ethanol. However other organic solvents may also be used such as ethyl acetate, diethyl ether, chloroform, methylene chloride, petroleum ether, acetone, pentane, or toluene.

Components of the extract were identified using gas chromatography-mass spectrometry (GC-MS) using an Agilent Technologies 6890N gas chromatograph equipped with an Agilent 5973 Network mass selective detector and an Agilent 7683 series autosampler.

The extract comprised the pentacyclic triterpene epi-lupeol. Other components of the extract were β-amyrin, α-amyrin, α-phellandrene dimers α-thujene and α-phellandrene. The extract has a GC-MS chromatogram as shown in FIG. 6 from which it can be seen that the main components are epi-lupeol, β-amyrin and dimmers of alpha-phellandrene.

Optionally, once the extract has been obtained it is dissolved in organic solvent, typically an alcoholic solvent such as methanol or ethanol, more usually ethanol and, ideally 100% ethanol at a concentration of about 10 mg/ml.

According to a further aspect of the invention there is provided an extract obtainable by the aforementioned method of the invention.

According to a further aspect of the invention there is provided a novel source of a pentacyclic triterpene such as epi-lupeol wherein said source is *Boswellia frereana*. Moreover the aforementioned source is also a source of β-amyrin, α-amyrin, α-phellandrene dimers, α-thujene and α-phellandrene. Further, the afore method provides a way in which said pentacyclic triterpene and β-amyrin, α-amyrin, α-phellandrene dimers, α-thujene and α-phellandrene can be extracted from the source.

BRIEF DESCRIPTION OF THE DRAWING FIGURES

The invention will now be illustrated by way of example only with reference to the following figures wherein;

FIG. 1 shows *Boswellia frereana* does not inhibit IL-1α/OSM-induced sGAG release from cartilage explants. *B. frereana* (100 μg/ml) did not affect sGAG levels in A. tissue, and B. cumulative release into the media from cartilage explants treated with 5 ng/ml IL-1α and 10 ng/ml OSM, over a 28 day period (DMMB assay). Data are expressed as mean sGAG per dry weight tissue (μg/mg)±SEM (n=4) (♦♦ $p<0.01$, ♦♦♦ $p<0.001$ for comparison between explants treated with IL-1α/OSM or left untreated;

FIG. 2 shows *Boswellia frereana* prevents IL-1α/OSM-induced collagen release from cartilage explants. *B. frereana* (100 μg/ml) had no effect on collagen levels in A. cartilage explants treated with 5 ng/ml IL-1α and 10 ng/ml OSM, however B. *B. frereana* inhibited collagen release into the media i.e. collagen degradation after 28 days of cytokine treatment (Hydroxyproline assay). Data are expressed as mean collagen per dry weight tissue (μg/mg)±SEM (n=4) (♦♦♦ $p<0.001$ for comparison between explants treated with IL-1α/OSM or left untreated, *** $p=0.001$ for comparison between explants treated with IL-1α/OSM+/−100 μg/ml *B. frereana*);

FIG. 3 shows IL-1α/OSM-induced MMP 9 expression/activation is inhibited by *Boswellia frereana*, as manifested by reduced MMP 9 transcription. *B. frereana* (100 μg/ml) inhibited expression of pro- and active-MMP 9, and reduced MMP 2 activation from cartilage explants treated with 5 ng/ml IL-1α and 10 ng/ml OSM. Representative gelatine zymograms from A. day 7 and B. day 28 only are analysed in this figure to maintain brevity, but the trends are representative of those observed at days 3, 14 and 21. Data are expressed as mean pro- or active-MMP (densitometric units) released per dry weight tissue (densitometric units/mg dry weight tissue)±SEM (n=4) (♦♦♦ $p<0.001$ for comparison between pro-MMP 9 released from untreated versus IL-1α/OSM explants; * $p<0.05$, *** $p<0.001$ for comparison between active-MMP 2 and pro-MMP 9, respectively, released from explants treated with IL-1α/OSM+/−100 μg/ml *B. frereana*). C. *B. frereana* partially suppressed cytokine-induced MMP 9 mRNA in explants treated for 3 days (qPCR). Data are presented as mean MMP 9 expression (arbitrary units)±SEM (n=4) ($p=0.079$);

FIG. 4 shows IL-1α/OSM-induced nitrite production and iNOS mRNA expression are suppressed by *Boswellia frereana*. A. *B. frereana* (100 μg/ml) significantly inhibited nitrite released from cartilage explants treated with 5 ng/ml IL-1α and 10 ng/ml OSM over the 28 day period (Griess assay). Data are expressed as mean nitrite released per dry weight tissue (μM/mg dry weight tissue)±SEM (n=4). B. iNOS mRNA levels were inhibited by *B. frereana* in cytokine-stimulated explants treated for 3 days (qPCR). Data are presented as mean iNOS expression (arbitrary units)±SEM (n=4) (♦♦ $p<0.01$, ♦♦♦ $p<0.001$ for comparison between explants treated with IL-1α/OSM or left untreated, and * $p<0.05$,  $p<0.01$, * $p<0.001$ for comparison between explants treated with IL-1α/OSM+/−100 μg/ml *B. frereana*);

FIG. 5 shows *Boswellia frereana* suppresses IL-1α/OSM-induced $PGE_2$ production, $PGE_2$ synthase and COX-2 mRNA expression. A. $PGE_2$ released from cartilage explants treated with 5 ng/ml IL-1α and 10 ng/ml OSM was significantly inhibited in the presence of 100 μg/ml *B. frereana* over a 28 day period ($PGE_2$ ELISA). Data are expressed as mean $PGE_2$ released per dry weight tissue (pg/mg dry weight tissue)±SEM (n=4). B. Cytokine-induced $PGE_2$ synthase and COX-2 mRNA levels were also suppressed by *B. frereana* in explants treated for 3 days (qPCR). Data are presented as mean gene expression (arbitrary units)±SEM (n=4) (♦ $p<0.05$, ♦♦ $p<0.01$, ♦♦♦ $p<0.001$ for comparison between explants treated with IL-1α/OSM or left untreated, and * $p<0.05$,  $p<0.01$, * $p<0.001$ for comparison between explants treated with IL-1α/OSM+/−100 μg/ml *B. frereana*);

FIG. 6 shows Epi-lupeol is the predominant constituent of *Boswellia frereana*. Identification of the major chemical constituents of the *B. frereana* ethanolic extracts using gas chromatography with mass spectrometry. A. Total ion current generated gas chromatograms, where the numbers correspond to the constituents identified. The y-axis of the top chromatogram has been expanded to show the volatile constituents obtained over an initial 50 minutes, B. The bottom chromatogram represents compounds identified over the entire 90 minute analysis. The largest peak (no. 18), and representing the major constituent, was identified as epi-lupeol accounting for almost 60% of the *B. frereana* extract. Trace amounts of other compounds including lupeol derivatives were also identified;

FIG. 7 shows total ion current (TIC) generated chromatograms for the Identification of: A) Essential oil extract of *B. frereana*. The major peak identified for the essential oil was α-Phellandrene dimer (11%) B) Hexane extract of *B. frereana* using gas chromatography-mass spectrometry (GC-MS). The major peak identified being epi-Lupeol (60%);

Figure 11:
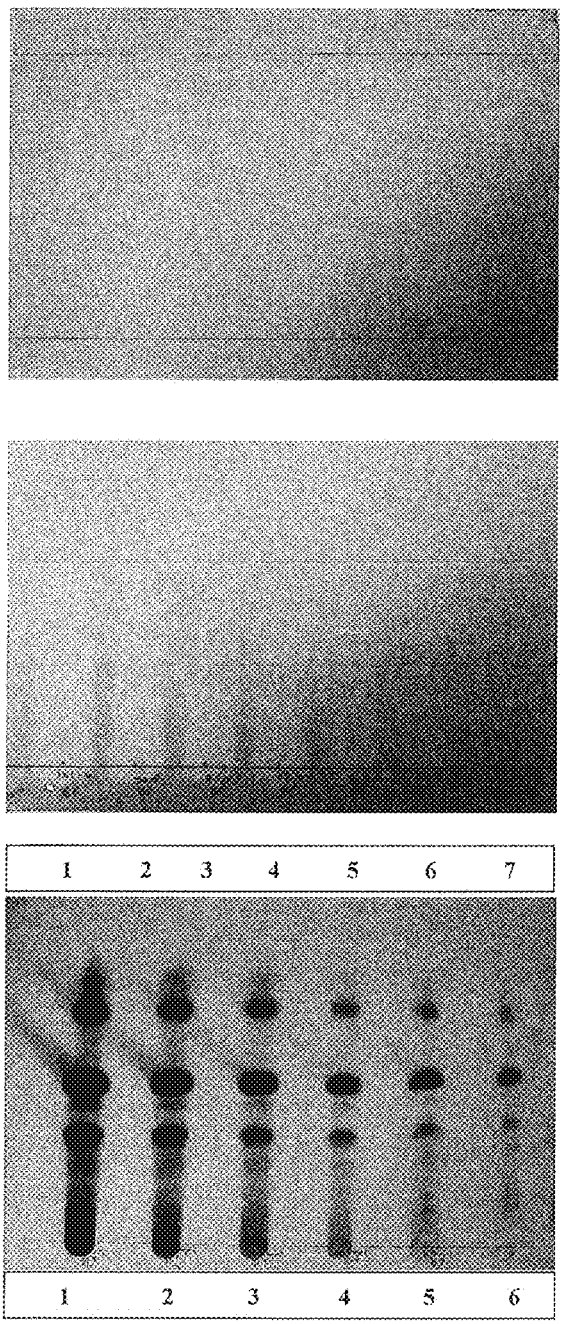

Beaker 1) *B. papyrifera*, Beakers 2-5) *B. frereana*, Beakers 6-7) *B. carteri*. *B. frereana* is the only species with hardly any amount of polysaccharide gum present;

FIG. 11 shows the anti-acetylcholinesterase activity of *B. Frereana* extract A) Control TLC plate without applying any samples to investigate false positives. B) TLC plate was spotted with 20 μl of *B. frereana* extracts at various concentrations and 20 μl of galanthamine hydrobromide. The following samples were applied: 1) 101.6, 2) 50.8, 3) 25.4, 4) 12.7, 5) 6.35, 6) 3.17 mg/ml, 7) galanthamine hydrobromide (1 mM). Both plates were developed with a mobile phase of toluene: ethyl acetate (90:10) and sprayed with 2.5 mM DTNB/2.5 mM ATCL in 50 mM Tris-HCl buffer (pH 8.0) followed by spraying with acetylcholinesterase enzyme solution (4 U/ml). AChE activity was observed as bright white spots on a yellow background. C) Detection of compounds present in the ethanol extracts of *B. frereana*. TLC plate was spotted with 20 μl of *B. frereana* extracts at various concentrations 1) 101.6, 2) 50.8, 3) 25.4, 4) 12.7, 5) 6.35, 6) 3.17 mg/ml. Plate was developed with a mobile phase of toluene: ethyl acetate (90:10) and sprayed with anisaldehyde detection reagent.

Figure 12:
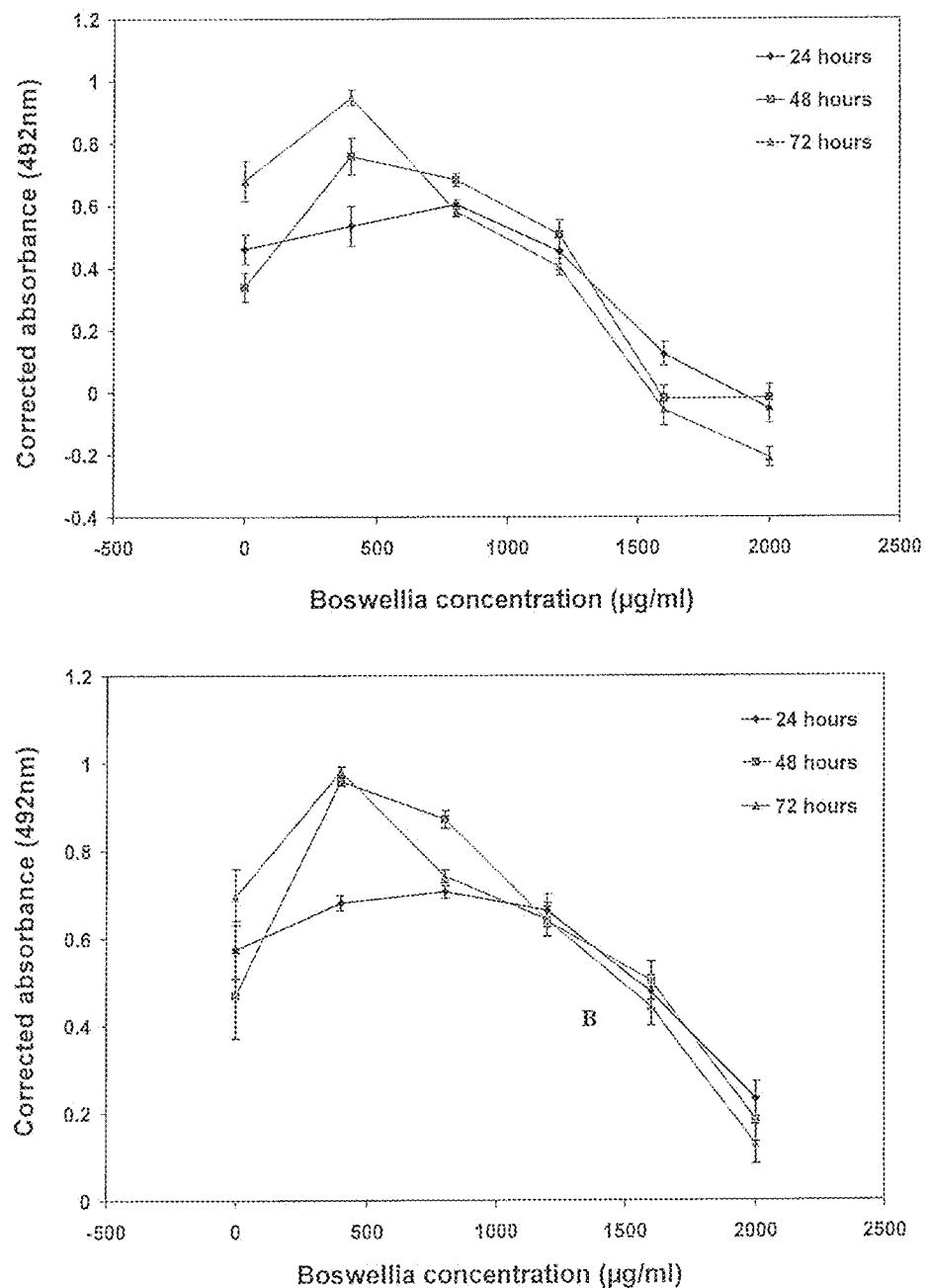

FIG. 12 shows the anti-tumour properties of *B. frereana* extracts on human cancer cells, particularly breast cancer cells of the MCF-7 breast cancer cell line, the two graphs show the effect of ethanolic *B. frereana* extract on MCF-7 cells at a range of 0-2000 μg/ml. Response was measured after 24, 48, and 72 hours by the absorbance of 8 wells. Cells were seeded at $5\times10^4$ cells/cm2 with 0.1 ml growth medium per well. *B. frereana* extract was added 24 hours after seeding. Ethanol concentration was adjusted in all wells to contain 0.77%. After a further 24, 48, and 72 hours and MTS assay. Absorbance was read using the FLUOstar OPTIMA.

Figure 13:
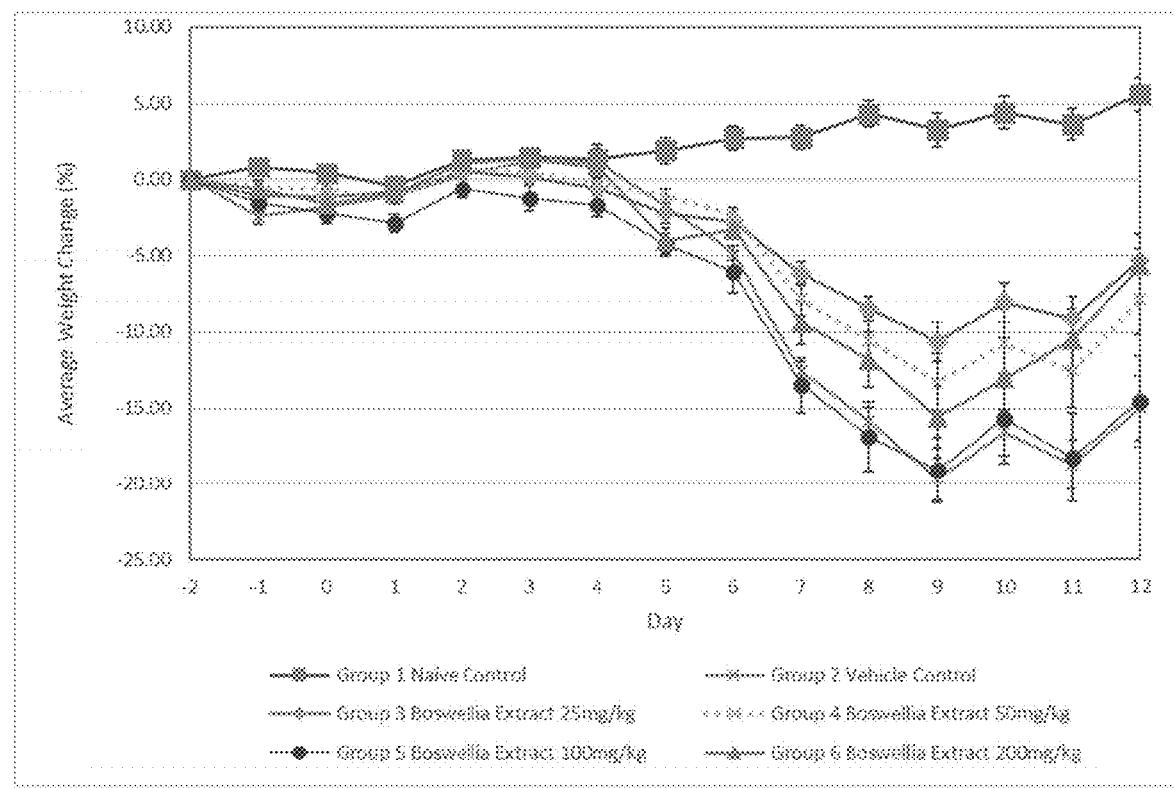

FIG. 13 shows mean percent body weight change in the mice model of induced IBD for various treatment groups. Animals were weighed daily and the percent weight change from Day −2 to Day 12 was calculated. Data represent group means±SEM. Significant differences were found by comparing all groups to the Vehicle Control Group using a one-way ANOVA followed by post-hoc Holm-Sidak's multiple comparison tests.

Figure 14:
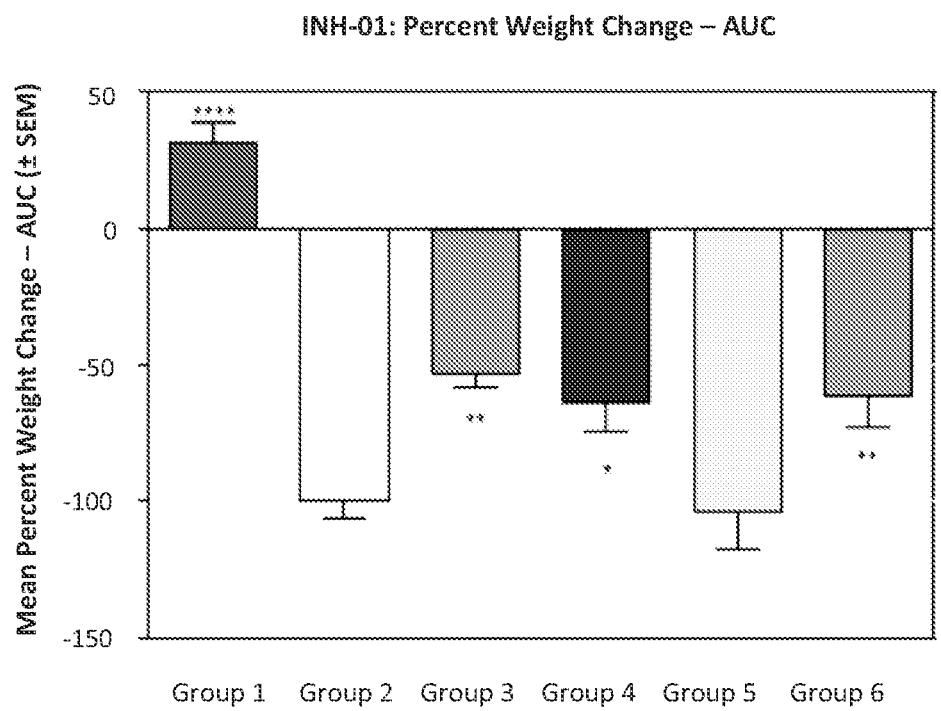

FIG. 14 shows mean percent body weight change Area Under the Curve (AUC) in the mice model of induced IBD for various treatment groups. The AUC was calculated for mean percent body weight change. Differences among the treatment groups in comparison to the Vehicle Control Group (Group 2) were evaluated using One-Way ANOVA followed by Holm-Sidak's multiple comparisons test. *$p<0.05$, $p<0.01$, **$p<0.0001$.

Figure 15:
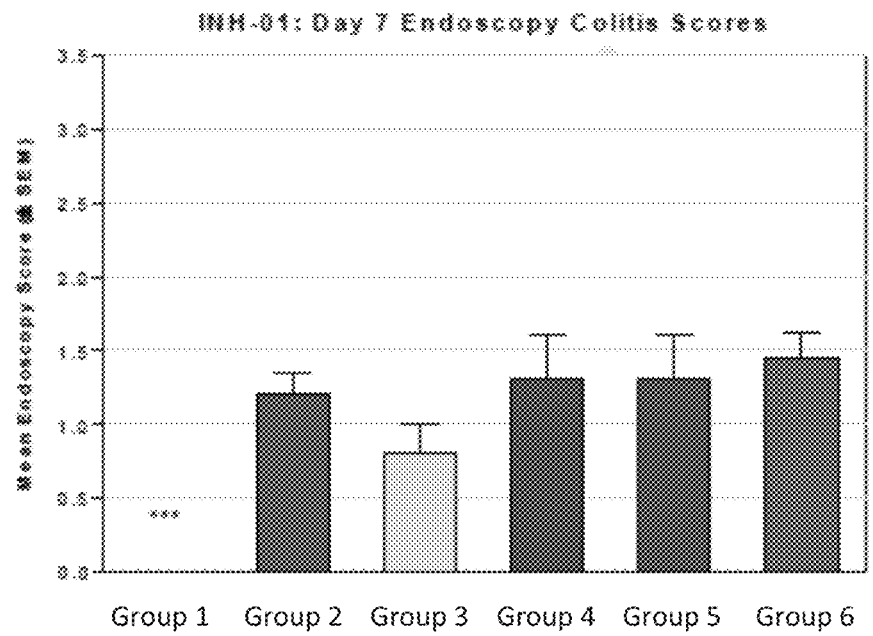

FIG. 15 shows Mean Endoscopy Colitis Scores on Day 7 of extract treatment groups in IBD. Animals underwent video endoscopy on Day 7 and colitis severity was scored on a scale of 0-4. Data represent group means and SEM. Significant differences were found by comparing the treatment groups to the Vehicle Control Group using a one-way ANOVA followed by post-hoc Holm-Sidak's multiple comparison tests. ***$p<0.001$.

Figure 16:
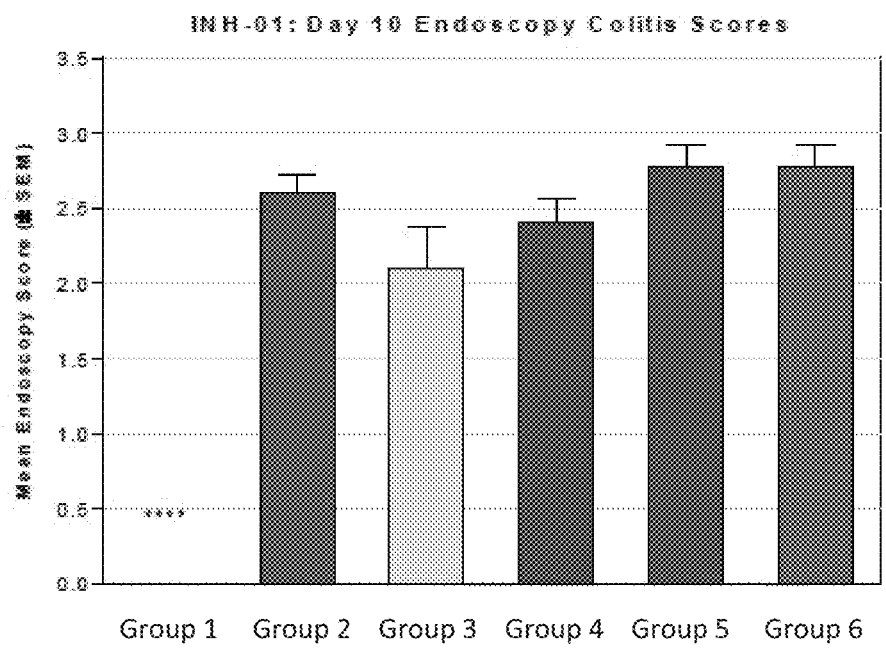

FIG. 16 shows Mean Endoscopy Colitis Scores on Day 10 of extract treatment groups in IBD. Animals underwent video endoscopy on Day 10 and colitis severity was scored on a scale of 0-4. Data represent group means and SEM. Significant differences were found by comparing the treatment groups to the Vehicle Control Group using a one-way ANOVA followed by post-hoc Holm-Sidak's multiple comparison tests. ****$p<0.0001$.

Figure 17:
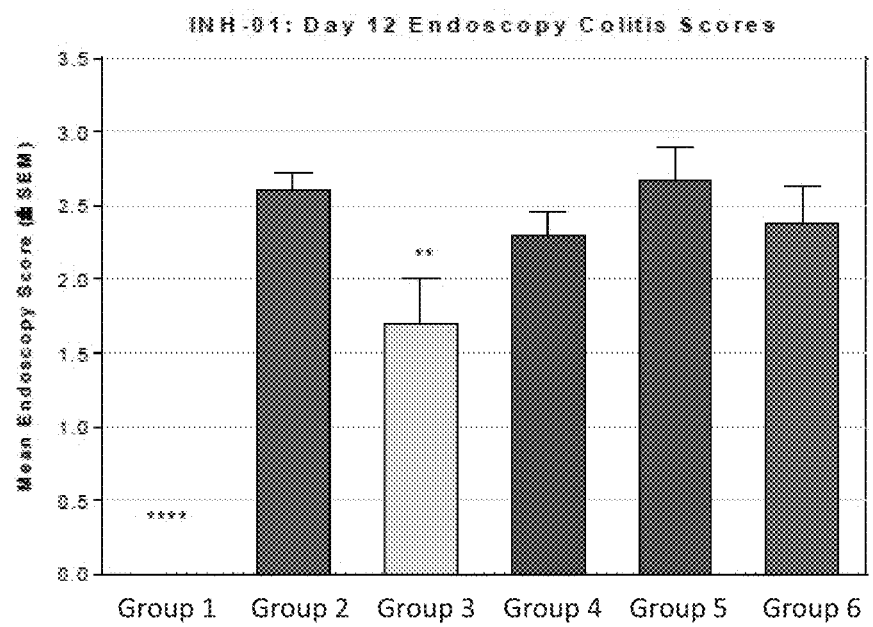

FIG. 17 shows Mean Endoscopy Colitis Scores on Day 12 of extract treatment groups in IBD. Animals underwent video endoscopy on Day 12 and colitis severity was scored on a scale of 0-4. Data represent group means and SEM. Significant differences were found by comparing the treatment groups to the Vehicle Control Group using a one-way ANOVA followed by post-hoc Holm-Sidak's multiple comparison tests. $p<0.01$, **$p<0.0001$.

Figure 18:
Figure 18:
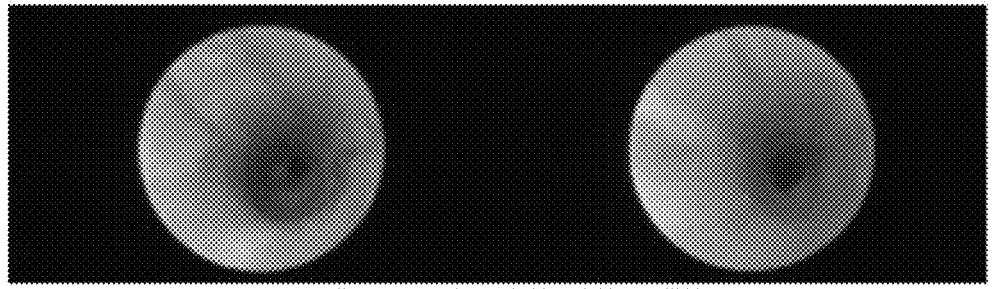
Figure 18:
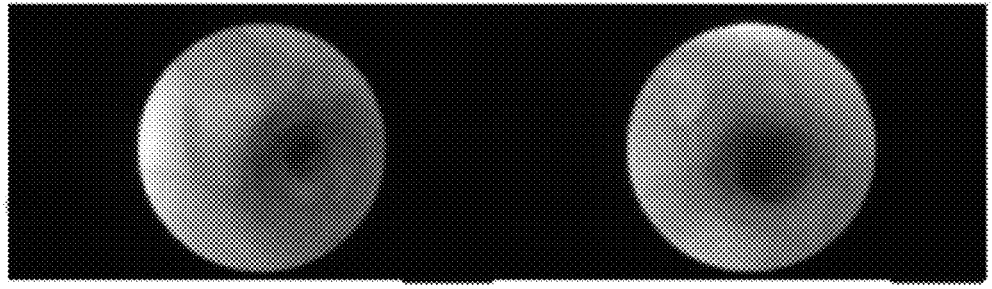

FIG. 18 shows representative endoscopy images on Day 7 of extract treatment groups in IBD. Naïve control, Vehicle control and Extract (25 mg/kg) treatment groups are shown. Animals underwent video endoscopy on Day 7 and colitis severity was scored on a scale of 0-4. Images were captured from each animal during the procedure and two representative images from each treatment group are presented.

Figure 19:
Figure 19:
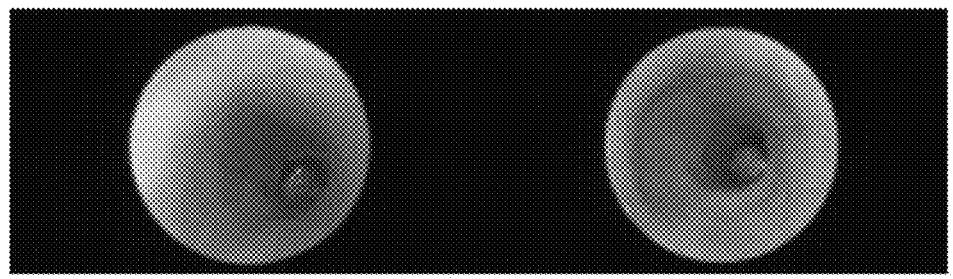
Figure 19:
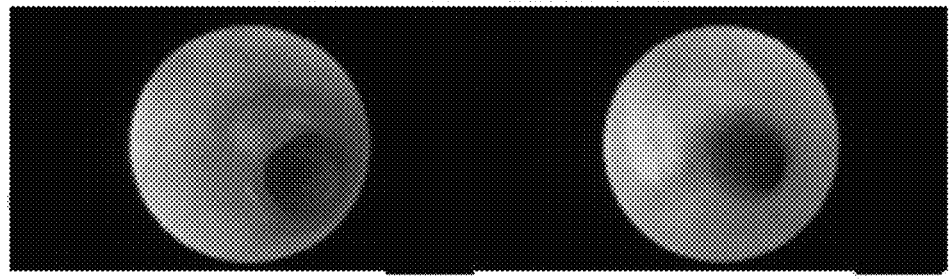

FIG. 19 shows representative endoscopy images on Day 7 of extract treatment groups in IBD. Extract (50 mg/kg, 100 mg/kg and 200 mg/kg) treatment groups are shown. Animals underwent video endoscopy on Day 7 and colitis severity was scored on a scale of 0-4. Images were captured from each animal during the procedure and two representative images from each treatment group are presented.

Figure 20:
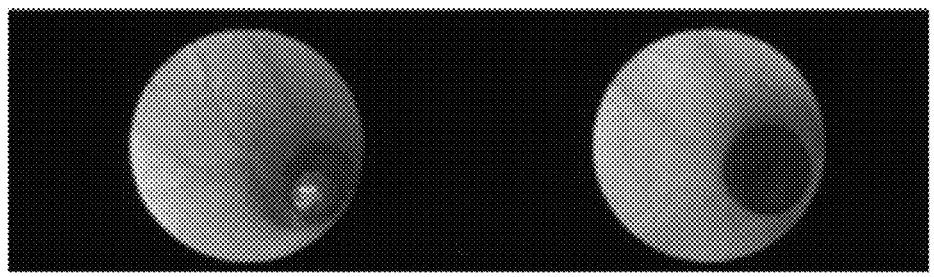
Figure 20:
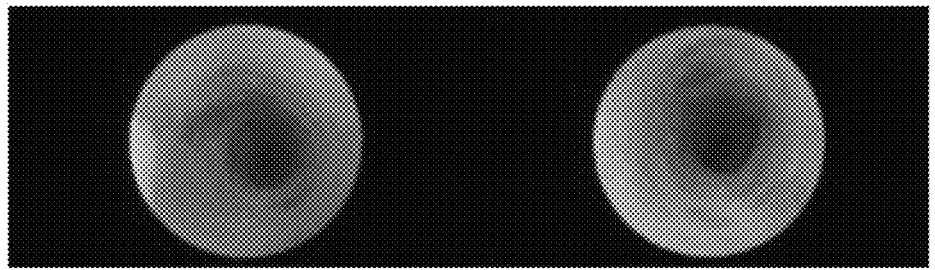
Figure 20:
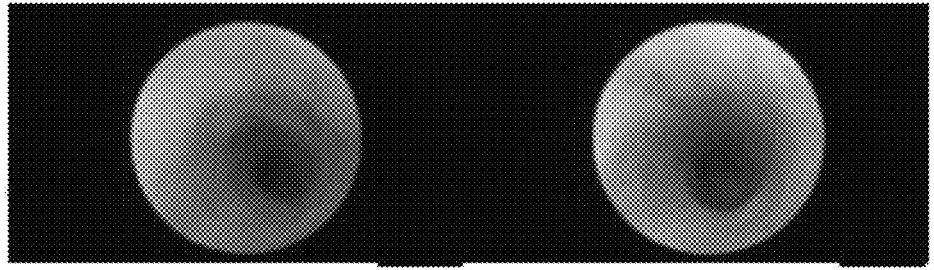

FIG. 20 shows representative endoscopy images on Day 10 of extract treatment groups in IBD. Naïve control, Vehicle control and Extract (25 mg/kg) treatment groups are shown. Animals underwent video endoscopy on Day 10 and colitis severity was scored on a scale of 0-4. Images were captured from each animal during the procedure and two representative images from each treatment group are presented.

Figure 21:
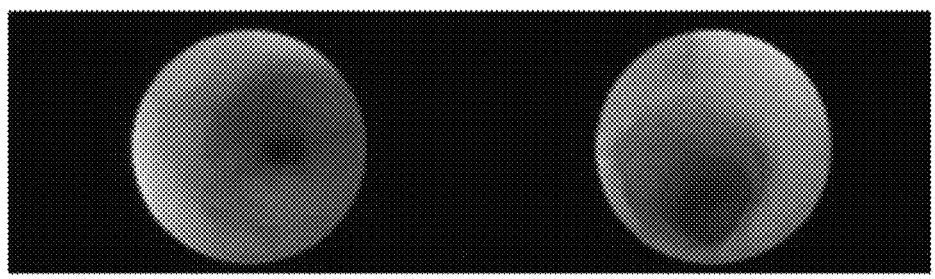
Figure 21:
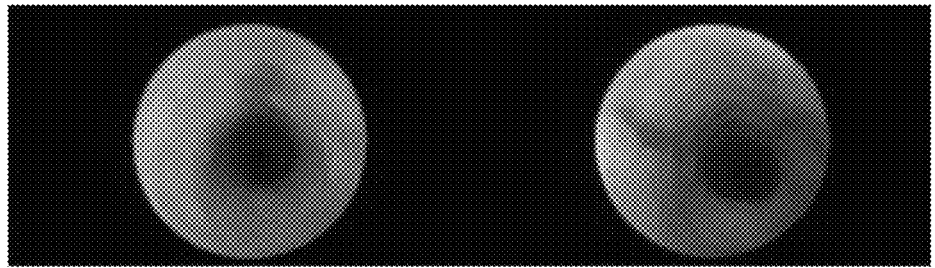
Figure 21:
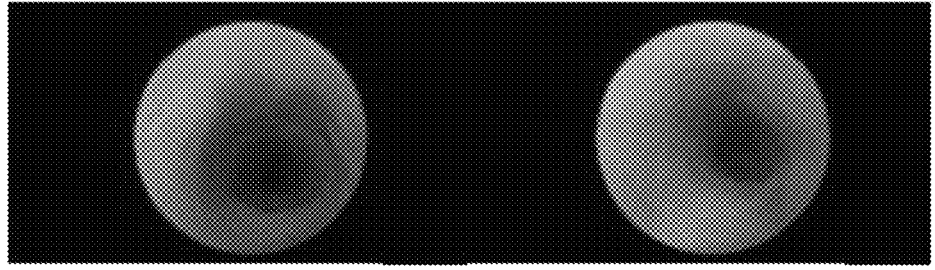

FIG. 21 shows representative endoscopy images on Day 10 of extract treatment groups in IBD. Extract (50 mg/kg, 100 mg/kg and 200 mg/kg) treatment groups are shown. Animals underwent video endoscopy on Day 10 and colitis severity was scored on a scale of 0-4. Images were captured from each animal during the procedure and two representative images from each treatment group are presented.

Figure 22:
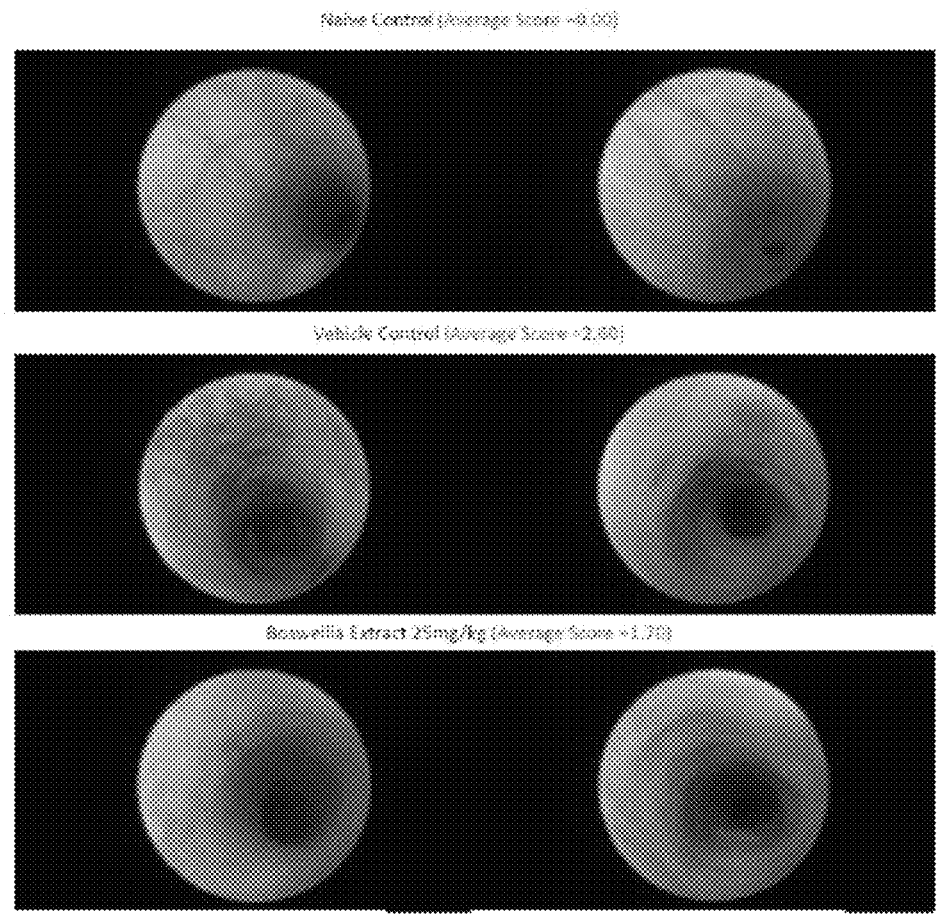

FIG. 22 shows representative endoscopy images on Day 12 of extract treatment groups in IBD. Naïve control, Vehicle control and Extract (25 mg/kg) treatment groups are shown. Animals underwent video endoscopy on Day 12 and colitis severity was scored on a scale of 0-4. Images were captured from each animal during the procedure and two representative images from each treatment group are presented.

Figure 23:
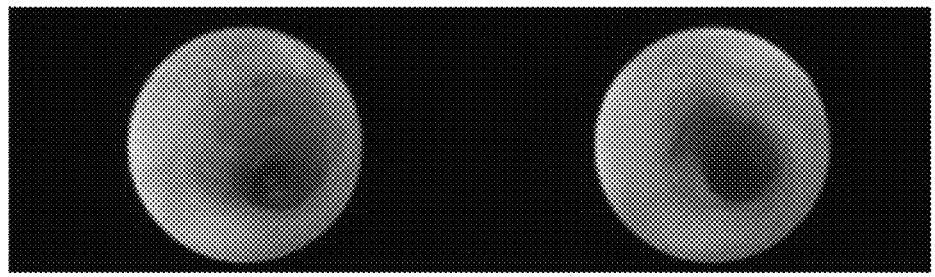
Figure 23:
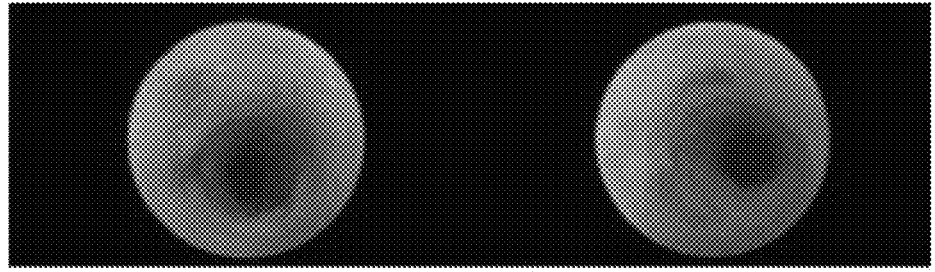
Figure 23:
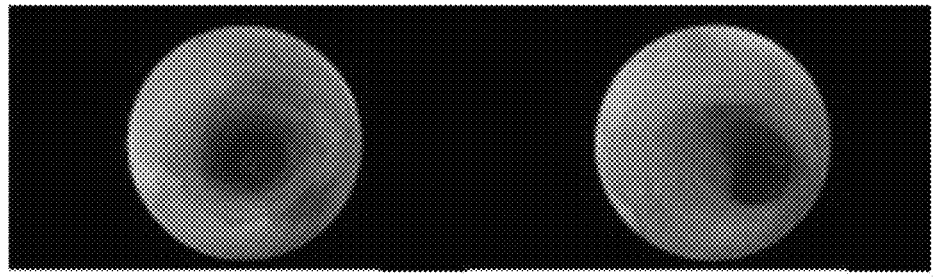

FIG. 23 shows representative endoscopy images on Day 12 of extract treatment groups in IBD. Extract (50 mg/kg, 100 mg/kg and 200 mg/kg) treatment groups are shown. Animals underwent video endoscopy on Day 12 and colitis severity was scored on a scale of 0-4. Images were captured from each animal during the procedure and two representative images from each treatment group are presented.

Figure 24:
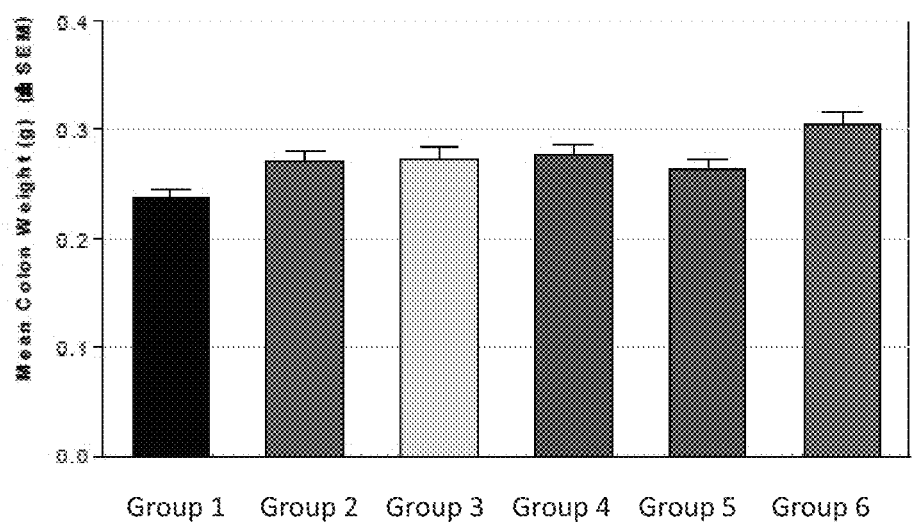

FIG. 24 shows mean colon weight of extract treatment groups in IBD on day 12. Mice were euthanized on Day 12 and colons were removed and weighed. Data represent group means and SEM. Significant differences were found by comparing the treatment groups to the Vehicle Control Group using a one-way ANOVA followed by post-hoc Holm-Sidak's multiple comparison tests.

Figure 25:
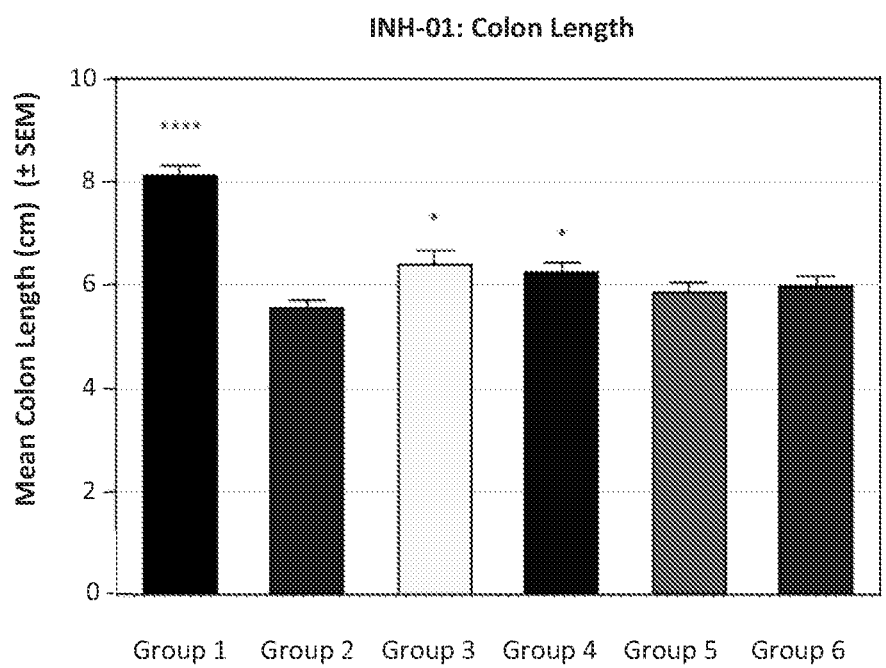

FIG. 25 shows mean colon length of extract treatment groups in IBD on day 12. Mice were euthanized on Day 12 and colons were removed and measured. Data represent group means and SEM. Significant differences were found by comparing the treatment groups to the Vehicle Control Group using a one-way ANOVA followed by post-hoc Holm-Sidak's multiple comparison tests. ****p<0.0001, *p<0.05.

Figure 26A:
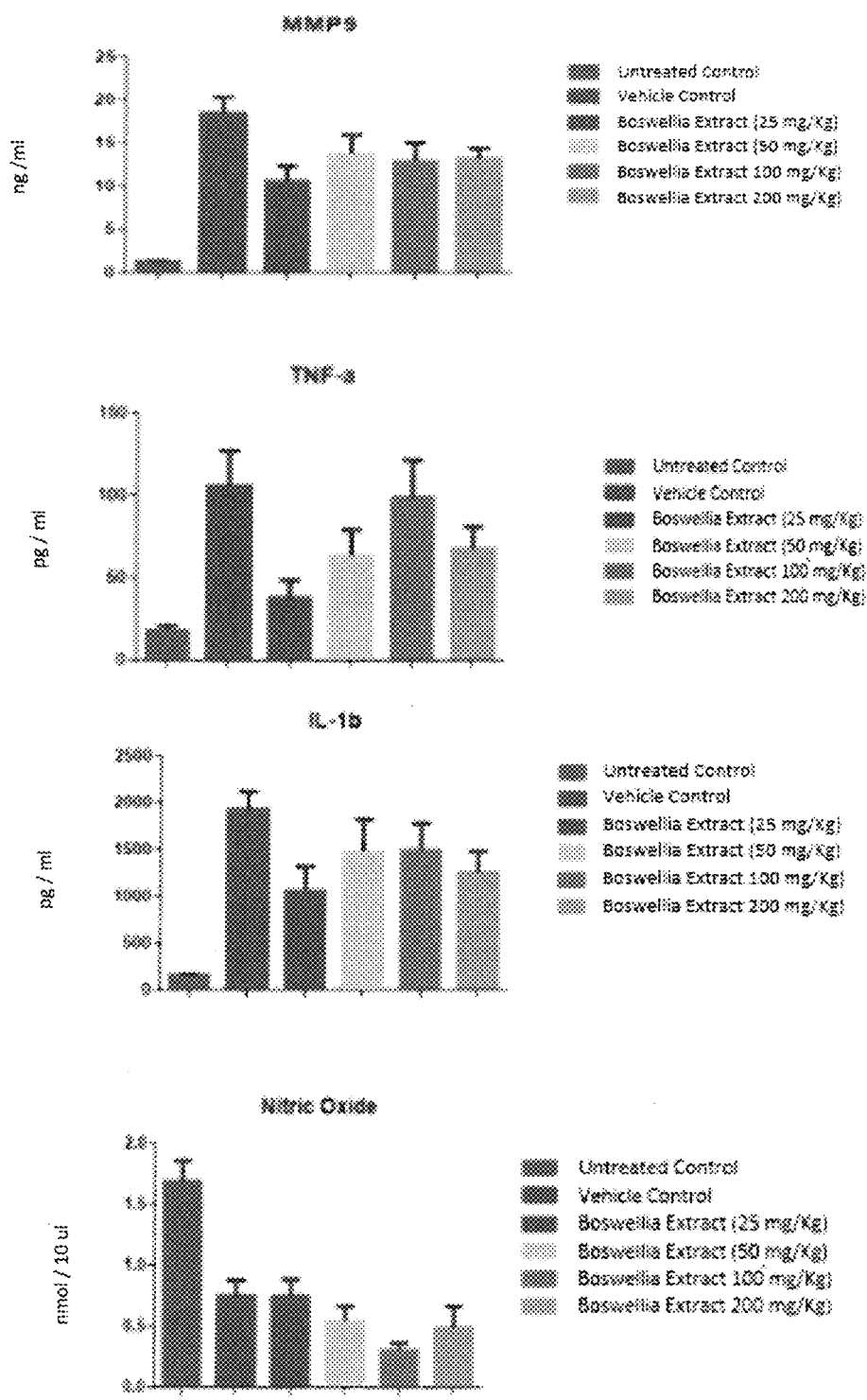

FIG. 26A shows the effect of various concentrations of the Boswellia extract (25/50/100/200 mg/kg) on a number of pro-inflammatory markers i.e. MMP9, TNF-α, IL-1b, and Nitric Oxide. The vehicle control contained corn oil and 3% DSS an inflammatory stimulant, hence it is a positive control and is expected to be higher than the untreated animals. At a selected concentration, all the B. frereana extracts are less than this control.

Figure 26B:
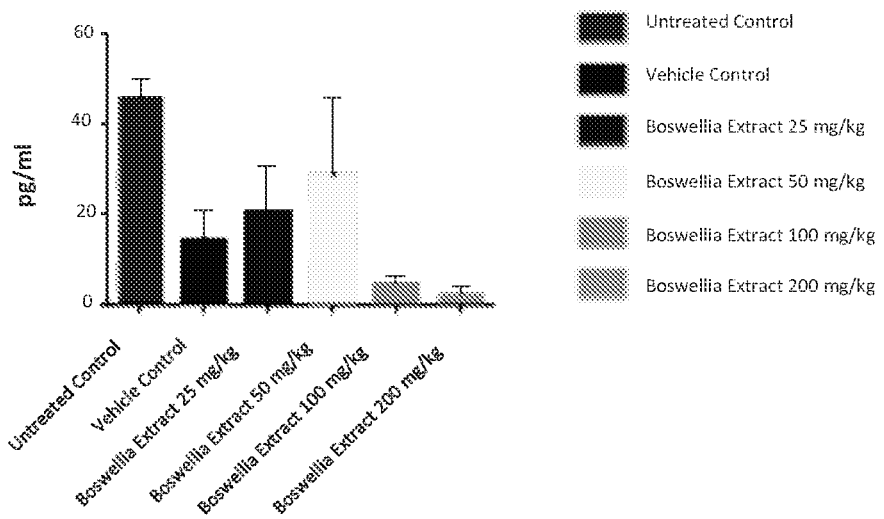

FIG. 26B shows the effect of various concentrations of the Boswellia extract (25/50/100/200 mg/kg) on the pro-inflammatory markers IL-2 and IFN-Gamma. The vehicle control contained corn oil and 3% DSS an inflammatory stimulant, hence it is a positive control and is expected to be higher than the untreated animals. At a selected concentration, all the B. frereana extracts are less than this control.

Table 1 shows the Primers used in quantitative PCR assays using SYBR Green® detection. Primers were designed to GenBank sequences using Primer 3 primer design software (www.frodo.wi.mit.edu/cgi-bin/primer3/primer3 www.cgi);

Table 2. Resin content of B. frereana oleoresin after extraction with hexane (nonpolar solvent) and ethanol (polar solvent);

Table 3. shows a comparison of the gum content of Boswellia frereana with related species;

Table 4 shows a summary of the components of B. frereana oleoresin;

Table 5 shows essential oil content of B. frereana oleoresin extracted by hydro-distillation;

Table 6 shows the chemical components identified in various extracts of B. frereana oleoresin (essential oil, hexane and ethanol);

Table 7 shows LD50 values of MCF-7 cells at 24, 48 and 72 h incubation;

Table 8 shows the IBD study design;

Table 9 shows the endoscopy colitis scoring scale;

Table 10 shows the percent of mice with DSS induced colitis exhibiting diarrhoea correlated with treatment; and Table 11 shows the percent of mice with DSS induced colitis exhibiting a bloody stool correlated with treatment.

DETAILED DESCRIPTION

Example 1

All reagents were purchased from Sigma (Poole, U.K.) unless otherwise specified. Culture medium consisted of Dulbecco's Modified Eagle's Medium (DMEM glutamax I™/HAMS F12 media (1:1), Invitrogen, UK) supplemented with 100 Units/ml penicillin, 100 µg/ml streptomycin, 50 µg/ml L-ascorbate-2-phosphate and 1× Insulin-Transferrin-Sodium selenite (ITS).

Somali frankincense oleoresins, Boswellia frereana (Somali name Maidi) and Boswellia carteri (Somali name Beyo) were procured from Hargeysa in Somaliland (northern Somalia). Ethiopian frankincense (Boswellia papyrifera) was kindly supplied by Mr Abdi Farah (Somaliland Frankincense Company, Cardiff). The solvents absolute ethanol and hexane (analar grade) were purchased from Fischer Scientific (Loughborough).

Extraction of Boswellia Frereana (for Bio-Assay)

Gum resin from Boswellia frereana was collected and the active component(s) prepared by extracting the gum resin (20 g) successively with ethanol (100%) for 7 days in a light-impermeable vessel. Insoluble gum resin was removed by filtration and the solvent evaporated at 60° C. More specifically, a known amount of B. frereana oleoresin (20 g) was accurately weighed, placed in a 500 ml glass beaker and 100 ml of ethanol added. The mixture was stirred with a spatula, covered with aluminum foil and para-film and then left to stand for seven days. The ethanol extract was filtered using a 150 ml Express™ Millipore filter. The solvent was evaporated under a gentle stream of nitrogen at a temperature of 60° C. The resulting B. frereana extract was dissolved in ethanol at a concentration of 10 mg/ml to give the working stock and stored at −20° C.

The chemical constituents of the B. frereana extracts were analysed by gas chromatography-mass spectrometry (GC-MS) using an Agilent Technologies 6890N gas chromatograph equipped with an Agilent 5973 Network mass selective detector and an Agilent 7683 series autosampler. (See FIG. 6). A scan range of 35 to 450 mass units was used for acquiring the mass spectra data with a sampling time of 2 which corresponds to 3.5 scans per second. Data acquisition was performed using the MSD Chemstation™ computer software. The identification of the individual peaks was conducted by comparing sample mass spectra to those stored in the National Institute of Standards and Technology (NIST) library database which contains over 54,000 spectra and by comparison of the sample mass spectra to published literature values.

National Institute of Standards and Technology is a physical science research laboratory and an agency of the U.S. Department of Commerce. (website—www.nist.gov). An alternative mass spec. library is commercially available from Wiley (website—www.sisweb.com/software/ms/wiley.htm#wiley8).

Chemical Characterisation: Comparison of the Resin and Gum Content of Oleoresins B. frereana B. Carteri and B. Papyrifera Boswellia oleoresin granules from B. carteri, B. frereana and B. papyrifera, were separately ground to a powder with a mortar and pestle. 40 g of each oleoresin powder was placed in separate 500 ml glass beakers and 100 ml of absolute ethanol added to each beaker. The mixtures were stirred with a spatula, covered with aluminum foil and para-film and then left to stand for three days. After this time period the ethanol extracts were stirred and then filtered under vacuum, using a 150 ml Express™ Millipore filter. The weight of ethanol insoluble gum (polysaccharide) left on each filter was recorded and the filtered ethanol extracts stored at −20° C.

Chemical Characterisation: Hexane Extraction of B. frereana

Gum resin from Boswellia frereana (20 g) was extracted using hexane as solvent for 3 days in a light-impermeable vessel. Insoluble gum resin was removed by centrifuging at 2000 rpm for 30 minutes and the clear supernatant layer removed. The hexane solvent was evaporated under a gentle stream of nitrogen at a temperature of 40° C. and stored at −20° C.

Chemical Characterisation: Essential Oil Extraction from *B. frereana* Oleoresins Deionised water (1 litre) was placed in a steam distillation apparatus, via the bottom glass vessel, and 50.6 g of *B. frereana* oleoresin placed in the top glass vessel. The two glass vessels were physically separated only by a perforated metal gauze. The heating mantle was set on maximum power and the water heated to boiling. The distillate (300 ml) was collected in a 500 ml glass container, 100 ml of hexane added and the mixture shaken. The hexane layer (top layer) was removed, transferred to a clean container and the solvent evaporated off under a gentle stream of nitrogen to yield an aromatic yellow oil (0.44 g).

In Vitro Model of Cartilage Degeneration

Full-depth articular cartilage (6 mm diameter explants) was harvested from the metacarpo-phalyngeal joint of 7-day old bovine calves using a biopsy punch. Cartilage explants were stabilised for 3 days in culture medium prior to treatment. An in vitro cartilage degradation model, as characterised by aggrecan loss and type II collagen proteolysis (29, 30), was established by treating cartilage explants with 5 ng/ml human recombinant IL-1α (Peprotech, U.K.) and 10 ng/ml human recombinant oncostatin M (OSM; Peprotech, U.K.), in the presence or absence of 100 µg/ml *B. frereana* extract; untreated explants served as a control. Cultures were maintained over a period of 28 days, with replenishment of media and/or treatments every 3 days. Tissue and media were harvested after 3, 7, 14, 21 and 28 days of culture. Cartilage explants were freeze dried over a period of 48 hours and all biochemical data normalised to dry weight of tissue (mg). For mRNA analysis, explants were cultured with the treatments indicated above for 3 days to allow investigation of early gene changes. Explants were snap frozen in liquid nitrogen prior to RNA extraction.

Cytotoxicity Assay: Cytotox 96®

Cell viability was assessed using the CytoTox 96® non-radioactive cytotoxicity assay (Promega) (31). The enzymatic assay quantitatively measures lactate dehydrogenase levels in culture medium as a consequence of cell lysis i.e. through cell death. Culture media (50 µl) was pipetted into a 96-well plate and mixed with 50 µl reconstituted substrate mix (kit component). After 30 minutes incubation at room temperature avoiding light, absorbance values were determined at 492 nm using a plate reader.

Analysis of Sulphated Glycosaminoglycans: Dimethylmethylene Blue (DMMB) Assay

Sulphated glycosaminoglycans (sGAG) levels in the tissue explants and released into the media was determined using the DMMB assay (32). Tissue explants (50 mg tissue: 1 ml buffer) were placed in digestion buffer (20 mM sodium phosphate (pH 6.8), 1 mM EDTA, 2 mM DTT) containing 300 µg papain (non-specific matrix proteinase). Samples were incubated at 60° C. for 1 hour, or until the tissue had completely dissolved. 10 mM iodoacetamide was added to the samples to alkylate the reactive sulphydryl groups (generated by DTT treatment) and the samples made up to a final volume of 5 ml (50 mM Tris (pH 8.0). A serial dilution was prepared using whale chondroitin-4-sulphate (sulphate C) with standards ranging from 0-50 µg/ml. Standards were prepared in the same buffer as the samples under analysis i.e. for media—DMEM-glutamax I™, and for tissue extracts—extraction buffer (50 mM Tris (pH 8.0)). 40 µl of standards and samples were pipetted in triplicate into a 96-well plate followed by addition of 2000 DMMB reagent (1.6% (w/v) 1,9-Dimethylmethylene Blue, 3% (v/v) sodium hydroxide, 1% (v/v) ethanol, 0.35% (v/v) formic acid). The plate was read immediately at a wavelength of 525 nm, and sGAG concentrations determined from reading directly off the standard curve. Any samples with a reading outside the limits of the standard curve were diluted in their respective buffer, the standards pipetted into fresh wells and the samples re-assayed.

Analysis of Collagen: Hydroxyproline Assay

The amount of collagen in and released from the cartilage was determined using the hydroxyproline assay using an adaptation of the method by Woessner (31). Briefly, tissue explants and media samples were hydrolysed in 12N or 6N HCl, respectively, at 110° C. for 24 hours and samples freeze-dried. A standard curve was prepared by dissolving 4-hydroxyproline in DMEM-glutamax I™ to give a range of 1-10 µg/ml. Hydrolysates (30 µl) and standards were added in triplicate to a 96-well plate followed by 70 µl diluent (66% (v/v) isopropanol) and 50 µl oxidant (18 mM chloramine T, 50% (v/v) stock buffer) before incubation at room temperature for 5 minutes. Colour reagent (3.7 mM dimethylamino benzaldehyde, 15% (v/v) perchloric acid, 85% (v/v) isopropanol) was added (1250 and incubated at 70° C. for 40 minutes. The absorbance was detected (540 nm) and the hydroxyproline content calculated from the standard curve. Any samples with a reading outside the limits of the standard curve were diluted in their respective buffer, the standards pipetted into fresh wells and the samples re-assayed. Total collagen was calculated by multiplying the hydroxyproline values by a factor of 7.14 (33).

Gelatin Zymography: Analysis of MMPs 2 and 9 Expression/Activation

The expression and activation of MMPs 2 and 9 were evaluated in experimental media samples by gelatin zymography (34). Media samples were denatured in a doubling dilution sample buffer (60 mM Tris (pH 6.8), 2% (w/v) SDS, 10% (w/v) glycerol, 0.01% (w/v) Bromophenol Blue) at 60° C. for 30 minutes. Briefly, samples were loaded onto a 7.5% (w/v) SDS polyacrylamide gel containing 0.5 mg/ml porcine gelatin (BDH, Poole, UK), and run in 1× Laemmli buffer (25 mM Tris, 0.192M glycine, 0.1% SDS) at 150V for approximately 60 minutes or until the dye front was nearing the end of the gel. Samples were loaded on an equivalent dry weight value taking into account differences in the volume of accumulated media over the 28 day culture. Gels were washed 3 times in 2.5% Triton X-100 to remove SDS and allow enzyme renaturation. Gels were incubated overnight in MMP proteolysis buffer (50 mM Tris (pH 7.8), 50 mM $CaCl_2$, 0.5M NaCl) at 37° C. to activate latent enzymes. Gels were subsequently stained (0.25% (w/v) Coomassie brilliant blue R-250, 10% (v/v) glacial acetic acid, 45% (v/v) methanol) for 1 hour. Cleared zones of gelatinolytic activity were observed upon destaining (7.5% (v/v) glacial acetic acid, 10% (v/v) methanol) for at least one hour or until zones of gelatinolysis were evident. Their relative quantities were analysed by scanning densitometry (UMAX magic scan) and NIH image software (NIH, Bethesda, Md.).

Griess Assay: Measurement of Nitrite Levels

Absolute concentrations of nitrite, a stable end-product of NO, were determined in the culture media using the Griess Assay (Promega). A nitrite standard curve was generated using a 0.1M sodium nitrite stock solution (kit component). The solution was diluted to a concentration of 100 µM (using $dH_2O$), and a two-fold serial dilution performed (standards ranging from 1.56 µM to 100 µM). Media samples (50 µl)

were pipetted in triplicate into a 96-well plate, 50 µl of sulphanilamide solution added and the plate incubated at room temperature for 10 minutes. NED solution (50 µl) was added to each well and the absorbance was detected at a wavelength of 540 nm. Nitrite (µM) was determined by comparison with the nitrite standard curve. Any samples with a reading outside the limits of the standard curve were diluted in their respective buffer, the standards pipetted into fresh wells and the samples re-assayed.

PGE$_2$ ELISA: Measurement of Prostaglandin E$_2$ Levels

PGE$_2$ production was measured in the culture media using a high sensitivity ELISA (PGE$_2$ HS-EIA; Cambridge Biosciences). PGE$_2$ standards were prepared from a 50 ng/ml stock solution (kit component) to give a standard curve ranging from 20 pg/ml to 640 pg/ml. Standards, negative controls and media samples (100 µl) were pipetted in triplicate into a 96-well plate followed by the addition of 50 µl of PGE$_2$ HS-EIA peroxidise conjugate. PGE$_2$ HS-EIA antibody (50 µl) was added to each well and the plate incubated overnight at 4° C. The contents of the plate were removed and the wells washed three times with 400 µl wash buffer (kit component). After removal of the wash buffer, 200 µl of pNpp substrate was added to each well and the absorbance measured at a wavelength of 450 nm using a plate reader. Absorbances were standardised by subtracting the absorbance of the negative control. A logarithmic plot of PGE$_2$ standards versus absorbance was performed, and the concentration of PGE$_2$ in the samples calculated. Any samples with a reading outside the limits of the standard curve were diluted in their respective buffer, the standards pipetted into fresh wells and the samples re-assayed.

RNA Extraction, cDNA Synthesis and Quantitative PCR Analysis

Cartilage explants were homogenised in 1 ml of Trizol™ Reagent (Invitrogen) in liquid N$_2$ (2000 rpm, 1.5 minutes) using a dismembrator (B. Braun Biotech Int., Germany), total RNA extracted and cDNA generated as previously described (35, 36). Briefly, 175 µl chloroform was added to the Trizol™ containing the homogenised cartilage, mixed by inversion several times and incubated at room temperature for 5 minutes. The RNA-containing phase was collected by centrifuging the samples (14,000 rpm, 15 minutes, 4° C.) and removing the upper aqueous component to a sterile eppendorf. An equal volume of isopropanol was added to the RNA-containing aqueous phase, the tube inverted several times to mix and the RNA precipitated overnight at −20° C. The RNA was pelleted by centrifuging the samples (14,000 rpm, 15 minutes, 4° C.); the supernatant was removed and the pellet washed with 1 ml 75% ethanol. The RNA was pelleted by centrifugation (14,000 rpm, 5 minutes, 4° C.), the supernatant discarded and the RNA-containing pellet air-dried at room temperature for approximately 30 minutes or until the ethanol had completely evaporated. Samples were DNase-treated (1 U DNase, 10% (v/v) DNase buffer) at 37° C. for 30 minutes. The residual DNase components were removed by adding 10% (v/v) DNA-later (Ambion) followed by centrifugation (10,000 rpm, 2 minutes) to pellet out the contaminants; the RNA remains in the supernatant. First strand cDNA was synthesised (20 µl reaction volume) using Superscript™ III reverse transcriptase (Invitrogen). Briefly, 1 µg random primers and 500 µM dNTPs were added to 10 µl RNA and incubated at 65° C. for 5 minutes. After adding 5× first strand buffer, 200 mM DTT and 10 U recombinant RNase Inhibitor (Promega), the sample was incubated at 42° C. for 2 minutes. 200 U Superscript™ III reverse transcriptase (Invitrogen) was added to the sample and incubated for 50 minutes at 42° C.; the reaction was terminated by heating the sample to 70° C. for 15 minutes. Real-time PCR was carried out using an Mx3000® QPCR System (Stratagene). A real-time qPCR assay, based on SYBR Green® detection, was designed for the transcriptional profiling of iNOS, PGE$_2$ synthase, COX-2 (37) and MMP 9 in the cDNA samples, after normalisation to the housekeeping gene 18S (38). Primers were designed to the open reading frame of iNOS, PGE$_2$ synthase and MMP 9 using Primer3 primer design software (frodo.wi.mit.edu/cgi-bin/primer3/primer3 www.cgi) (Table 1). Briefly, 12.5 µl of Sybr® Green Jumpstart™ Taq ReadyMix buffer was added to 100 nM of each primer and 10 cDNA and the reaction made up to a final volume of 25 µl with dH$_2$O. Samples and negative controls (omitting cDNA template) were loaded into a 96-well microplate (Stratagene) and the PCR reaction controlled by MxPro™ qPCR software. All reactions were carried out at an annealing temperature of 60° C. Relative quantification was calculated using the $2^{-\Delta\Delta C_T}$ method as described previously (39, 40), using the untreated controls as a reference group to quantify relative changes in target gene expression. The data are presented as fold change in gene expression normalised to an endogenous reference gene 18S relative to the untreated control cDNA samples. Where there was no amplification of a gene product in the untreated cartilage cDNA samples, the fold change in gene expression was relative to the IL-1α/OSM treated cDNA samples.

Statistical Analysis

Data were normalised to the dry weight of the cartilage explants and presented as mean±standard error mean (n=4 explants per treatment). Each experiment was repeated three times and representative data are shown. Data were tested for normality (Anderson-Darling) and equal variances prior to parametric analyses (Minitab). Statistical analysis was performed using a 2-factor generalised linear model ANOVA and Tukey's post hoc test, or where indicated in the text using a 2-sample t-test (qPCR analysis). Differences were considered significant at P values less than 0.05.

*Boswelia Frereana* Extracts: Acetylcholinesterase (AChE) Inhibition Assay

Thus TLC method for screening AChE activity is based on that reported by Rhee et al (56) and is a modified version of Ellman's original UV method for determining AChE activity (Ellman et al., 57).

Chemicals and Reagents

Acetylcholinesterase (AChE, 1000 U) from electric eel, Trizma base, Acetylthiocholine iodide (ATCI), 5,5'-Dithio-bis-(2-nitrobenzoic acid) (DTNB, Ellman's reagent) and Galanthamine hydrobromide were all purchased from Sigma-Aldrich (Poole, Dorset). Toluene and ethyl acetate were purchased from Fisher Scientific (Loughborough, Leicestershire).

Preparation of Buffer Solution (50 mM Tris-HCl at pH 8)

6.057 g of Tris base (molecular weight 121.14 g) was accurately weighed into a 1 litre volumetric flask. 800 ml of deionised water was added, it's pH adjusted to pH8 with concentrated HCl and then diluted to volume with de-ionised water. Buffer was stored at 4° C.

Preparation of Acetylcholinesterase Iodide (2.5 mM)/5,5'-Dithiobis-(2-Nitrobenzoic Acid) (DTNB) (2.5 mM) Spray Mixture 72.2 mg of ATCI and 100.8 g of DTNB were accurately weighed into the same 100 ml volumetric flask and diluted to volume with buffer and stored at 4° C.

Preparation of Acetylcholinesterase Enzyme Solution (4 U/ml)

The contents of AChE vial (1000 U) was transferred to a 250 ml volumetric flask and siluted to volume with buffer. Solution was stored at a −20° C. until required.

Sample Preparation

A stock solution of *Boswellia frereana* ethanol extract (101.6 mg/ml) were diluted in ethanol yielding final *B. frereana* concentrations of 101.6, 50.8, 25.4, 12.7, 6.35 and 3.17 mg/ml.

Reference Standard Preparation (1 mM)

Galanthamine hydrobromide (10 mg) was accurately diluted with 27 ml of methanol.

TLC Plate

A silicagel 60 $F_{254}$ with the dimensions 200 mm×200 mm and thickness 0.2 mm was purchased from VWR International (West Sussex).

TLC Development Solvent 90 ml of toluene and 10 ml of ethylacetate were added together and mixed together.

Detection Reagent 0 5 ml of anisalaldehyde was transferred to a 100 ml volumetric flask and 10 m! of glacial acetic acid added. To this 85 ml of methanol was added followed by 5 ml of concentrated sulphuric acid and then shaken to mix.

Procedure

100 µI of the *Boswellia* extracts were applied to the Tic plates as well as 100 µl of galantamine hydrobromide (1 mM) as a reference solution. The TIC plate was developed using toluene and ethyl acetate (90:10) as the solvent. After drying for 30 minutes the plate was sprayed with 20 ml of the substrate/dye mixture (ATCI/DTNB) until saturated. The plate was allowed to dry for 5 minutes before spraying with 20 ml of the enzyme solution and then allowed to dry. The plate was photographed within 10-20 minutes although the white spots remained for 1 hour. A positive spot was obtained if a white spot was observed on a yellow background. A control TLC plate (with no samples) was developed, to investigate false positives, and treated as described for the treated TLC plates. TLC components were also detected by spraying developed TLC plates with anisaldehyde solution.

Anti-Tumour Properties of *Boswellia frereana* Extracts on Human Breast Cancer Cell Lines (MCF7)

Research was carried out using the human breast cancer cell line MCF-7 (donated by Dr Richard Clarkson, Cardiff University, originally from ECACC). The human breast cancer cell line MCF-7 was established in 1970 from the pleural effusion from a 69 year old Caucasian female suffering from a breast adenocarcinoma (58). This cell line has been used extensively as an experimental tumour model.

Maintenance of MCF-7 Cell Cultures

MCF-7 cells were grown in Minimum Essential Medium Eagle (EMEM) with Earle's balanced sat solution without L-glutamine (Lonza) which was supplemented with 1% glutamine (Invitrogen), 0.1% insulin (Sigma), 1% Penicillin and streptomycin (Invitrogen), 10% foetal bovine serum (Sigma), 1% non-essential amino acids (Lonza) and 1% sodium pyruvate (Ambrex). They were grown in adherent culture using 75 $cm^2$ flasks (Costar) at 37° and in an atmosphere of 5% $CO_2$ in air.

Cells were sub-cultured every 7 days and seeded at $2 \times 10^4$ cells per $cm^2$. To harvest the cells, first the culture medium was removed. Next the cell layer was gently rinsed with approximately 7 ml of 0.25% trypsin with EDTA (Gibco) to remove any remaining growth medium. Then a further 5 ml of trypsin/EDTA was added and the flask was incubated for 3 minutes to separate the cells and detach from the surface of the flasks. An inverted microscope (Nikon Diaphot) was used to check that the cells have detached. 10 ml of medium was then added to the flask and gently pipetted up and down to separate the clumps of cells. The cells were counted using a Bright Line haemocytometer cell counting chamber and seeded into flasks containing a total of 20 ml of medium each. Flasks were then placed into the incubator to allow cells to stick. Medium was changed once a week.

Measurement of Cell Response Using the MTS Assay

The CellTiter 96 Aqueous Non-Radioactive Cell Proliferation Assay (Promega) kit was used to perform the MTS assays. The kit contains 20 ml MTS solution and 1 ml PMS solution.

All MTS assays were performed in 96 well plates (Costar). The cells were seeded at 1 $0.2 \times 10^3$-$1.5 \times 10^5$ cells/$cm^2$ with 0.1-0.2 ml of appropriate growth media. Control wells in all cases contained the same volume of medium, the same volume of test reagent and the same volume of MTS solution but contained no cells. The plates were then incubated. Cell suspension and MTS solution were added to the wells using either a repetitive pipette (HandyStep) or a multi-channel pipette and trough (Transferpette). Ceil suspension in the trough was regularly stirred with a sterile spatula to avoid cells settling to the surface, 24-48 hours after seeding 50 µl of test reagent was added as appropriate. 24-168 hours after seeding MTS solution was added at 20 µl MTS solution per 100 µl of medium to the wells with and without cells. The plates were then returned to the incubator for two hours. Next the plates were removed from the incubator and shaken using an orbital plate shaker (MSI Minishaker IKA) for ten seconds to ensure the reaction product was evenly distributed in the well. The absorbance was then read at 492 nm using either an Anthos reader 2001 (Labtech) plate reader or a FLUOstar OPTIMA (Labtech) plate reader. In the case of the growth curves the medium was changed at 72 hours and every 24 hours following this so that medium depletion would not act as a confounding variable. To remove the medium from the wells a sterile swab was placed on top of the plate which were then both inverted. The medium was absorbed by the sterile swab and any remaining medium was removed by dabbing on another sterile swab. Fresh medium (0.2 ml) was then pipetted into all of the test and control wells.

Preparation of *B. frereana* (*Boswellia frereana*) Ethanol Extract

An ethanol extract of *B. frereana* (3.01778 g) was dissolved in 10 ml of absolute ethanol (Fisher Scientific) to give a stock solution of 266.7 mg/ml. This was then filtered using a Sartorius PTFE membrane (Fisher Scientific UK) to ensure sterility. The stock solution was diluted in medium to give 3 times the final concentration needed and 50 µl of this concentrate was added to wells containing 0.1 ml of medium to give a final concentration of 88-2000 ug/ml in the well. The samples were then vortexed to disperse the extract in the medium. The ethanol concentration was adjusted to be constant in all wells. The concentration was adjusted to contain the same concentration as the well containing the highest concentration of the *B. frereana* extract. This ranged from 0.17-0.77%

Non-specific background absorbance can occur in culture medium incubated with MTS solution. This was corrected for using control wells which were identical to test wells but contained no cells. The average absorbance from these control wells was subtracted from all other test well absorbance values to yield corrected absorbance. These corrected absorbance values were used to plot formazan absorbance on the graphs. Error bars express standard error of the difference (se(d)) between the test wells and control wells and were calculated using the following equation:

$$se(d)=sqrt(se_t^2+se_c^2)$$

se(d)=standard error of the difference;
sqrt=square root;
$se_t$=standard error of the test wells;
$se_c$=standard error of the control wells.

Calculating $LD_{50}$ Values $LD_{50}$ values were calculated as the concentration of the *B. frereana* extract at which there was a 50% reduction in formazan absorbance. Graphs were plotted using the mean formazan absorbance and were displayed as a percentage of the absorbance at 0 μg/ml. The $LD_{50}$ was taken at 50% formazan absorbance at each sampling time (24, 48 and 72 hours after incubation with *B. frereana* extract) on the curves. This was done for each experiment and the average at each incubation time was recorded in the results.

Statistical Analysis

Statistical analysis was performed in Minitab 15.

Two-way ANOVA and three-way ANOVA were performed by means of the general linear model, Tukey simultaneous pair wise comparison was used to compare the means. If the variances were not homogeneous (as verified using the Bartlett's test) a weighted regression was used. The weights used were the reciprocal of the variance (59)

Results

Surprisingly the *B. frereana* oleoresin was found to be almost completely soluble in both hexane and ethanol resulting in very high extraction yields for the resin (99%), as indicated in table 2.

Tables 2 and 3 indicate that *B. frereana* oleoresins contain very little ethanol insoluble gum (polysaccharide). This is in contrast to other species of *Boswellia* such as *B. carterii* and *B. papyrifera*, where the ethanol insoluble gum fraction comprised 48% and 51% respectively as shown in table 2. *Boswellia* oleoresins from India (*B. serrata*) has also been reported to contain a substantial amount of alcohol insoluble gum fraction, in the region of 24% (55).

Unlike the oleoresins from *B. carteri, B. serrata* and *B. papyrifera* this particular species of *Boswellia* (*B. frereana*) was found not to be amenable to steam distillation due to its low gum content. On contact with the steam the resin softened and completely passed through the perforated gauze and into the hot water. The method for isolation of the essential oil was therefore in actuality one of hydro-distillation rather than steam distillation.

The essential oil content of *B. frereana*, using hydro-distillation was quite low (0.87%) as indicated in table 5.

Figure 7:
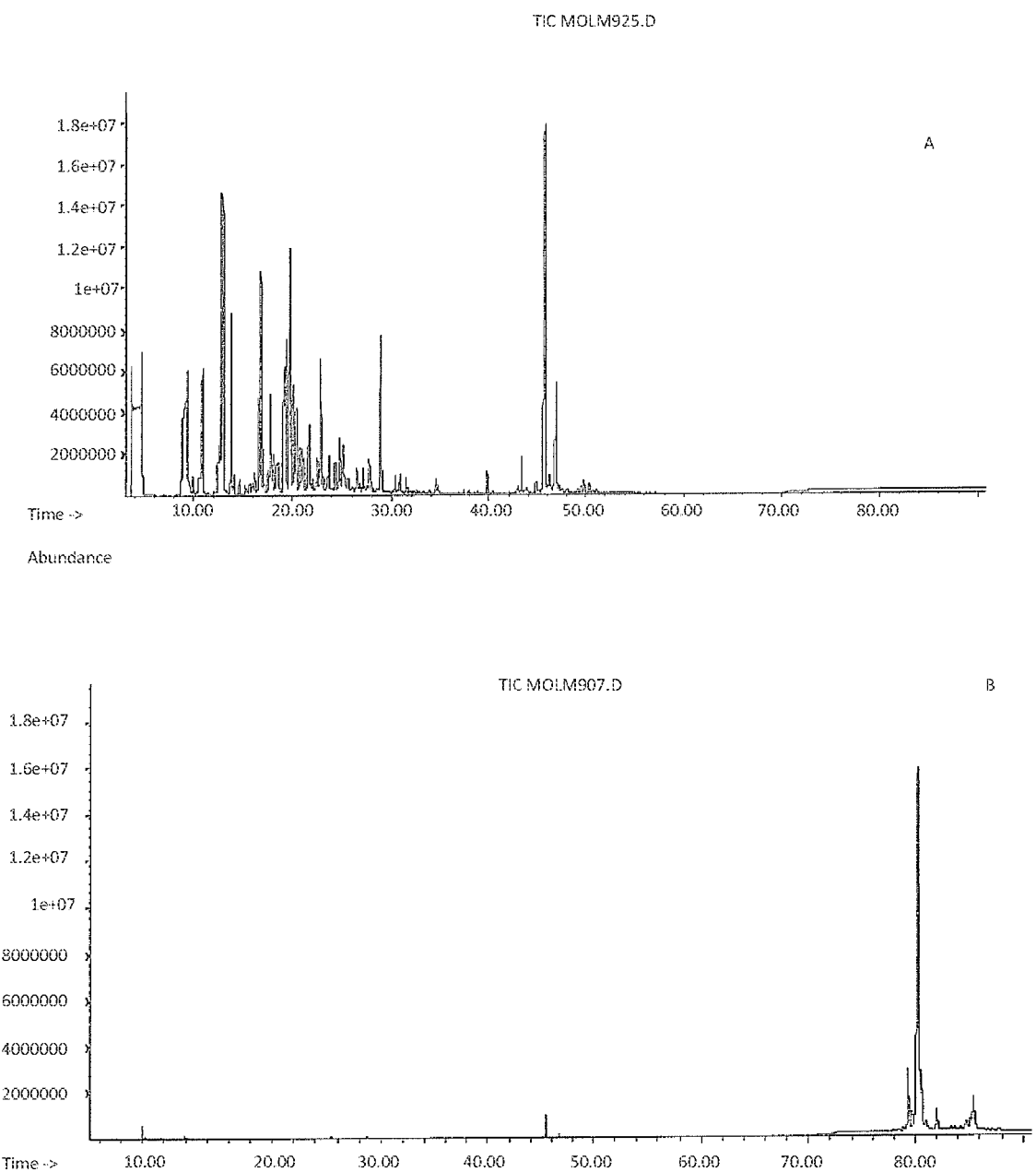
Figure 8:
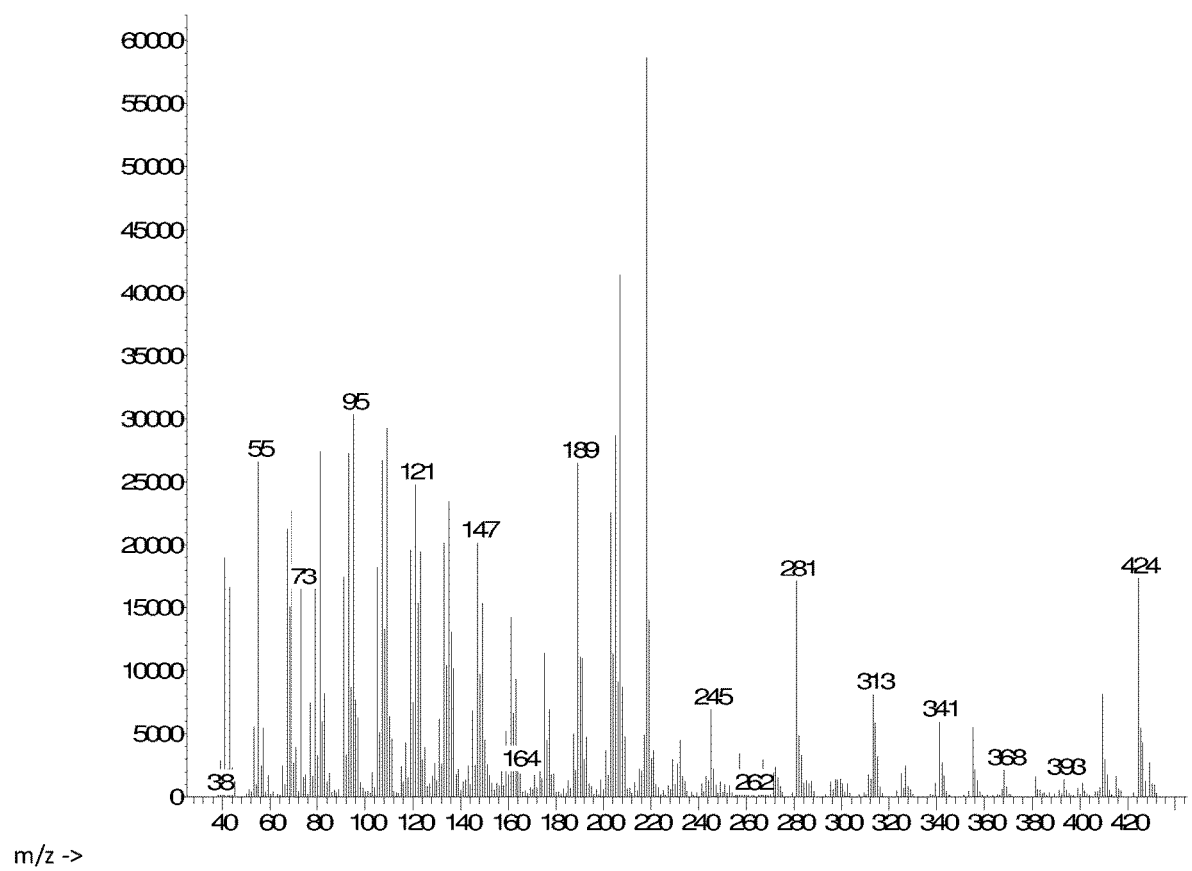
FIG. 8 shows mass spectrum (EI+ve) of epi-Lupeol obtained at retention time 79.99 minutes.
Figure 9:
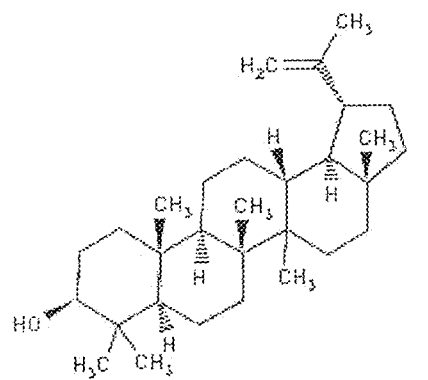
FIG. 9 shows chemical structures of commonly occurring terpenes present in *B. frereana*.
Figure 9:
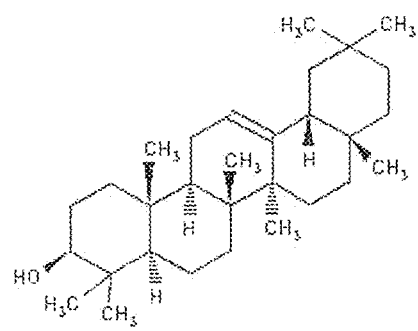
Figure 9:
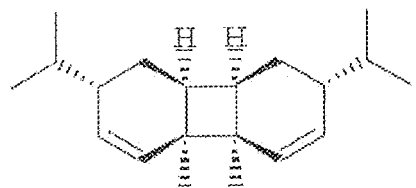
Figure 10:
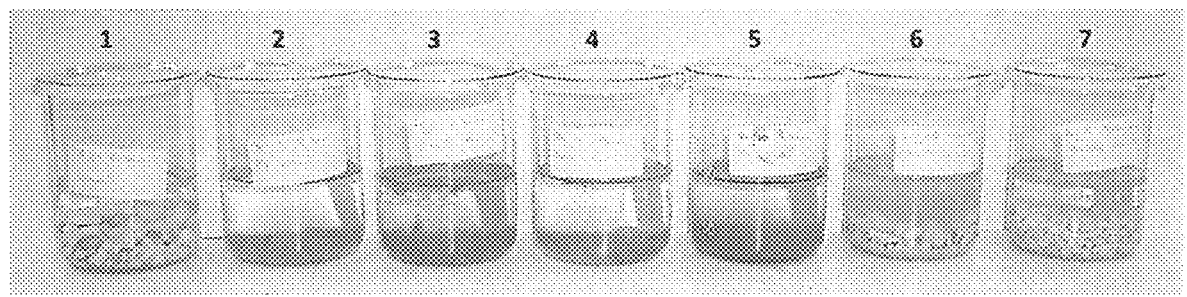
FIG. 10 shows ethanol extracts of three *boswellia* species illustrating different gum contents.

Non-polar solvents such as hexane are commonly used, in phytochemistry, to extract the volatile oil component from oleoresins whilst ethanol is commonly used to extract the more polar resin fraction of oleoresins. We have previously used hexane to isolate the volatile oil component of related aromatic oleoresins such as frankincense (*B. carterii, B. papyrifera*), Opoponax (*Commiphora guidotti*) and myrrh (*Commiphora molmol*) whilst leaving the resin and gum content of the oleoresins intact. Unexpectedly, in this case, hexane is not suitable for the extraction of the volatile oil component of *B. frereana* as the solvent also extracted the resin component. See FIG. 7.

*B. frereana* does not Affect Cartilage Chondrocyte Viability.

Treatment of cartilage explants with 5 ng/ml IL-1α and 10 ng/ml OSM or 100 μg/ml *B. frereana*, separately or in combination did not significantly affect cell viability over the 28 day culture period (data not shown).

*B. frereana* does not Affect sGAG Levels in an In Vitro Model of Cartilage Degradation.

Figure 1:
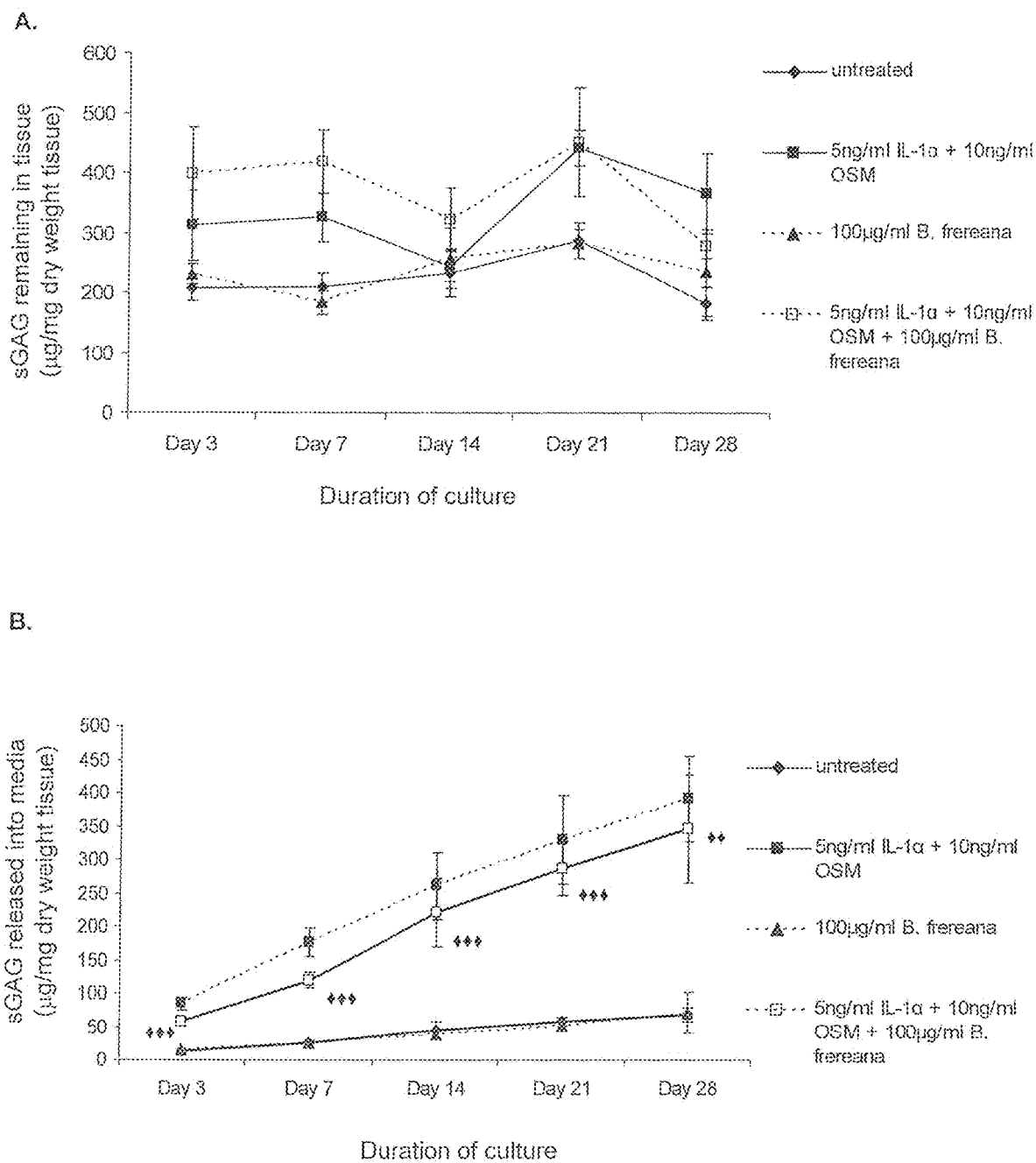

Treatment of explants with 5 ng/ml IL-1α and 10 ng/ml OSM, separately or in combination with 100 μg/ml *B. frereana* had no effect on sGAG levels in the tissue (FIG. 1A). In contrast there was a significant increase in the amount of sGAGs detected in the media of explants treated with IL-1α/OSM relative to those that were left untreated or treated with *B. frereana* alone (p<0.01; log transformation required for analysis of days 3 and 7 data). *B. frereana* did not rescue cytokine-induced sGAG loss from the cartilage explants over the culture period (FIG. 1B).

*B. frereana* Reduces Collagen Release in an In Vitro Model of Cartilage Degradation.

Figure 2:
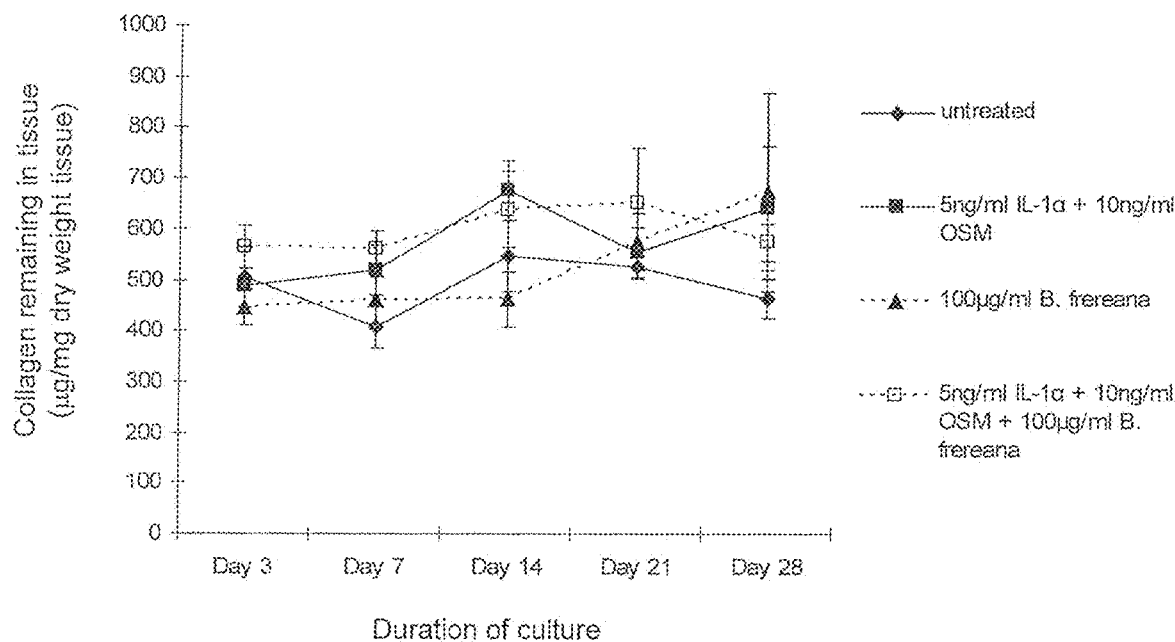
Figure 2:
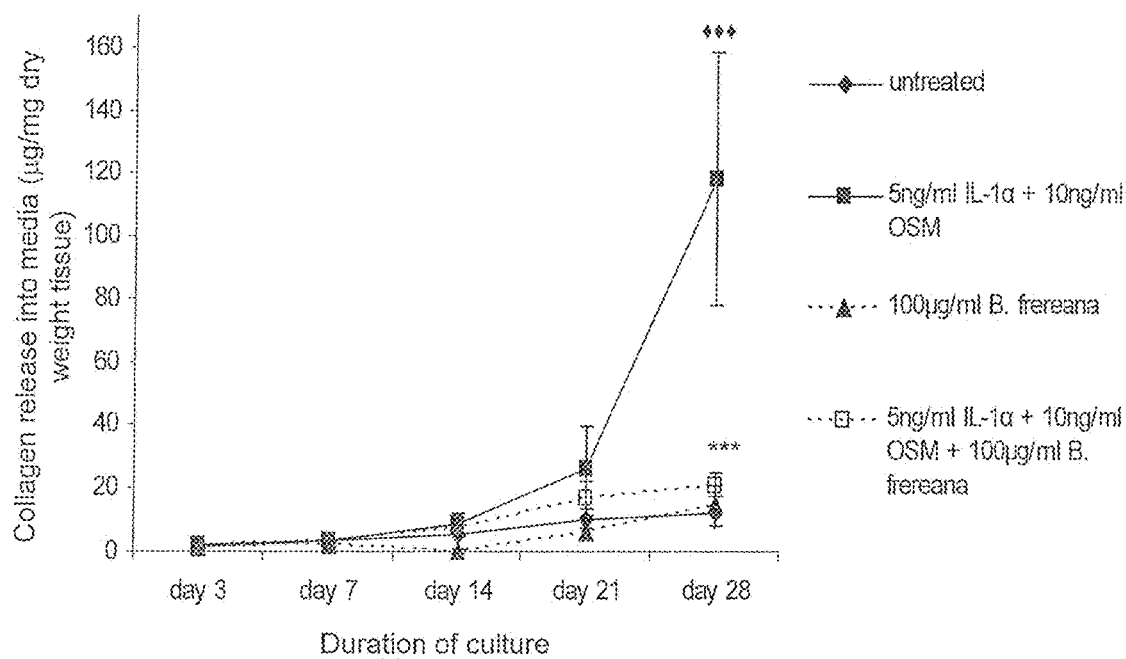

There were no appreciable differences in the amount of collagen measured in the explants across treatments (FIG. 2A). Significantly more collagen was released into the media from cartilage explants treated with IL-1α/OSM after 28 days in culture compared to the untreated or *B. frereana* treated explants (p=0.001; log transformation). However, there was a significant reduction in collagen released from cartilage explants treated with IL-1α/OSM in combination with *B. frereana* (p=0.012; log transformation) returning levels to basal amounts (FIG. 2B).

*B. frereana* Inhibits Cytokine-Induced MMP 9 Expression and Activation, Due to a Reduction in MMP 9 Transcription, in an In Vitro Model of Cartilage Degradation.

Figure 3:
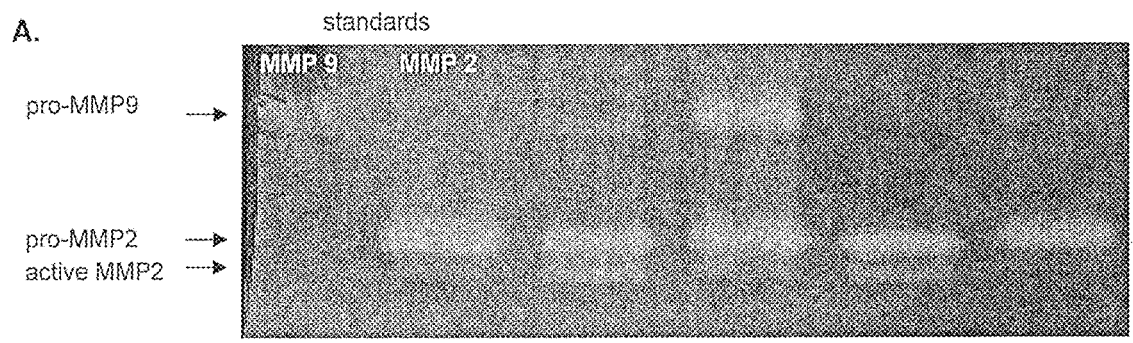
Figure 3:
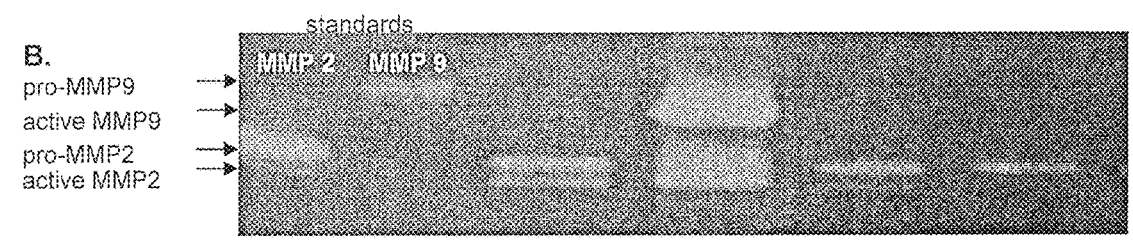

In untreated explants, there was minimal expression of pro-MMP 9 after 7 days, but pro- and active-MMP 2 were observed in both the untreated and *B. frereana* treated explants (FIG. 3A). IL-1α/OSM-stimulated cartilage synthesised significantly higher levels of pro-MMP 9 after 7 days (p<0.0001; log transformation). Active-MMP 9 was not observed at this time point. Pro- and active-MMP 2 levels did not alter appreciably after IL-1α/OSM stimulation. Interestingly, *B. frereana* inhibited cytokine-induced pro-MMP 9 synthesis (p<0.0001; log transformation), but had no effect on the expression or activation of pro-MMP 2. After 28 days in culture, pro-MMP 9 was no longer observed in the untreated cartilage explants, but both pro- and active MMP 2 were present (FIG. 3B). These observations were also evident in cartilage treated with *B. frereana*. Overall, *B. frereana* abolished cytokine-induced MMP 9 expression and activation. There was a dramatic reduction in the amount of pro-MMP 9 expressed by the explants treated with IL-1α/OSM in combination with *B. frereana* which was highly significant from day 7 onwards. As a consequence of reduced MMP 9 synthesis, levels of active MMP 9 were abolished bringing expression levels back to that of untreated explants. It also appeared to reduce IL-1α/OSM-mediated pro-MMP 2 expression but this did not reach significance (p=0.06; log transformation). However, *B. frereana* did significantly counteract the activation of pro-MMP 2 by IL-1α/OSM (p=0.04; ranked log transformation). Only media removed from explants after 7 and 28 days have been included in the manuscript to maintain brevity but are representative of the trends observed over all of the time points. As MMP 9 protein expression was sensitive to treatment, MMP 9 mRNA levels were quantified in tissue which had been treated for 3 days (FIG. 3C). MMP 9 mRNA was below the limit of detection in both untreated and *B. frereana* treated cartilage explants. However, *B. frereana* reduced IL-1α/OSM-induced MMP 9 transcription by almost 50%, although this did not quite reach significance (p=0.079; 2-sample t-test).

*B. frereana* Reduces Cytokine-Induced Nitrite Production and Supresses iNOS mRNA Expression in an In Vitro Model of Cartilage Degradation.

Figure 4:
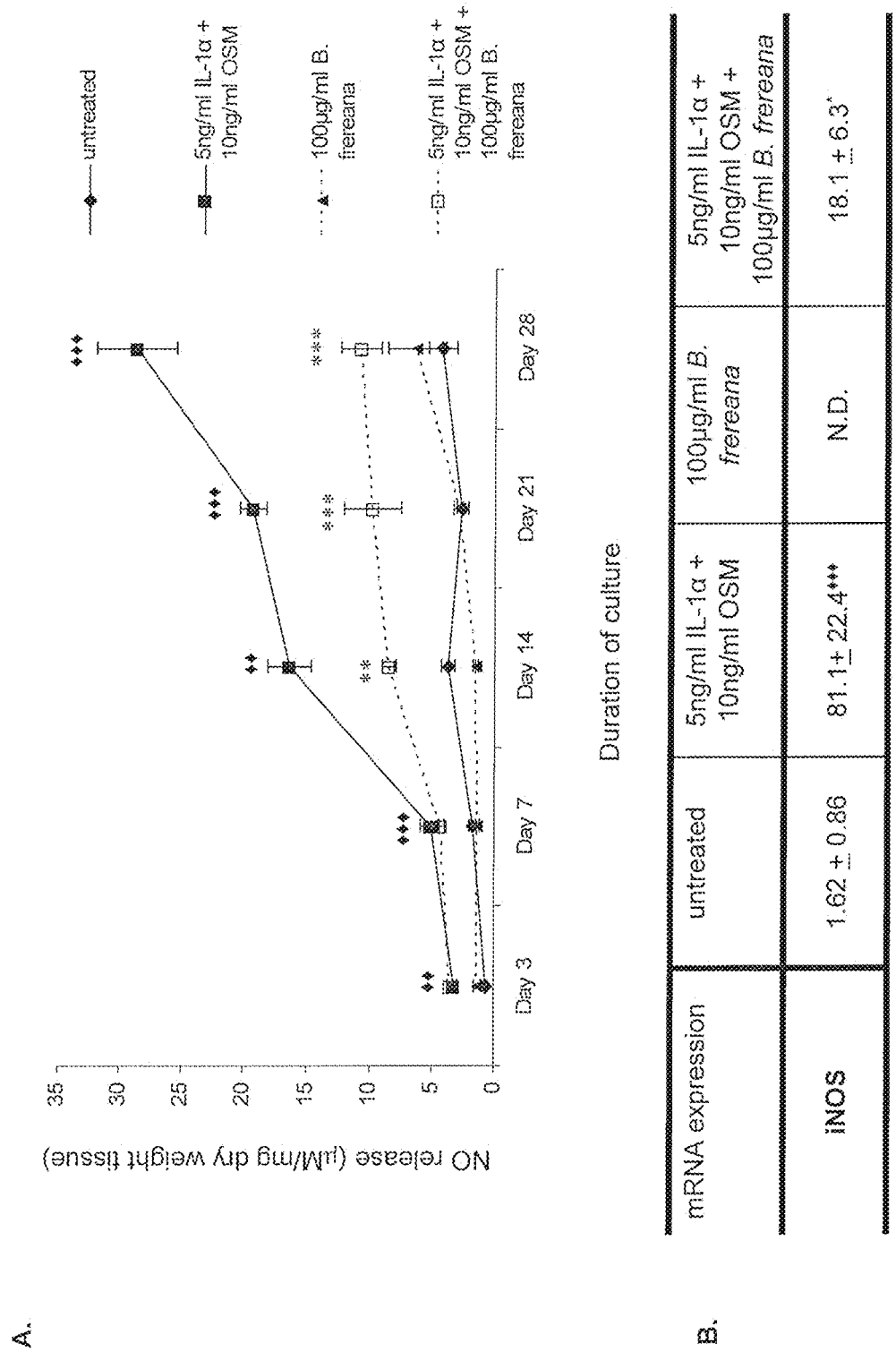

The amount of nitrite produced by the untreated explants, and explants treated with *B. frereana* was low (<5 μM/mg dry weight tissue) and did not change appreciably over the 28 day culture period (FIG. 4A). As expected, cytokine treatment significantly increased production of nitrite after 3 ($p<0.0033$), 7 ($p=0.0009$), 14 ($p<0.0029$), 21 ($p<0.0001$) and 28 days ($p<0.0001$) relative to untreated explants (log transformation of data), but *B. frereana*, significantly inhibited IL-1α/OSM induced nitrite production after 14 ($p=0.003$), 21 ($p=0.0007$) and 28 days ($p=0.001$) (log transformation of data). iNOS mRNA expression levels were quantified to determine whether the reduction in nitrite at the later time points might be attributed to transcriptional inhibition early on in the culture period (FIG. 4B). There were variable but minimal amounts of iNOS mRNA in untreated cartilage explants after 3 days in culture. iNOS mRNA was not detected in cartilage treated with *B. frereana*. As expected, there was an approximate 50-fold increase in iNOS mRNA levels in IL-1α/OSM-stimulated explants relative to the untreated controls ($p<0.0001$; log transformation), which was reduced by approximately 75% in the presence of *B. frereana* ($p=0.02$; log transformation), consistent with the levels of nitrite observed in the culture media.

*B. frereana* Reduces Cytokine-Induced $PGE_2$ Production and Supresses Both $PGE_2$ Synthase and COX-2 mRNA Expression in an In Vitro Model of Cartilage Degradation.

Figure 5:
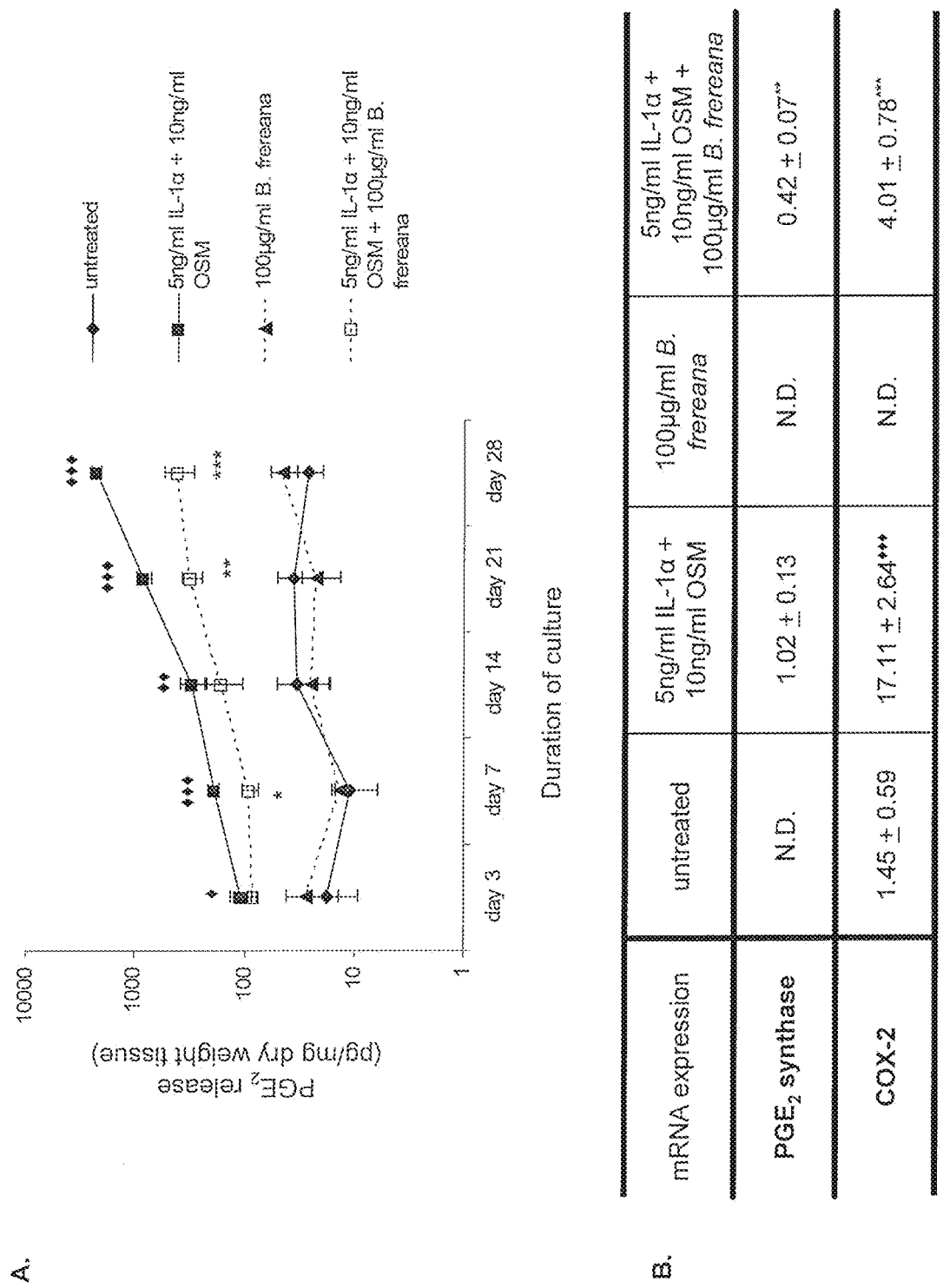

The amount of $PGE_2$ produced by the untreated explants and explants treated with *B. frereana* did not change appreciably over the 28 day culture period (<25 pg/mg dry weight tissue) (FIG. 5A). As expected, cytokine treatment significantly increased $PGE_2$ production after 3 ($p=0.012$; log transformation), 7 ($p=0.0002$), 14 ($p=0.006$; log transformation), 21 ($p<0.0001$; log transformation) and 28 days ($p<0.0001$; log transformation) relative to untreated explants, ranging from 100-1000 pg/mg dry weight tissue. In the presence of *B. frereana*, there was a significant inhibition of IL-1α/OSM-induced $PGE_2$ production in explants after 7 ($p=0.03$), 21 ($p=0.005$; log transformation) and 28 days of treatment ($p=0.0005$; log transformation); however this did not return to basal levels. $PGE_2$ synthase mRNA expression levels were also quantified to determine whether the reduction in $PGE_2$ observed over the culture period might be attributed to inhibition of $PGE_2$ synthase transcription (FIG. 5B). $PGE_2$ synthase mRNA was not detectable in either the untreated cartilage or in the tissue treated with *B. frereana* after 3 days of culture. IL-1α/OSM stimulated $PGE_2$ synthase mRNA expression in the cartilage, and this was reduced by almost 60% when cytokine-stimulated explants were co-treated with *B. frereana* ($p=0.007$; 2-sample t-test). In conjunction, mRNA levels of COX-2—the rate-limiting enzyme in $PGE_2$ synthesis was also quantified. Minimal amounts of COX-2 mRNA were observed in untreated cartilage, and levels were undetectable in cartilage treated with *B. frereana* (FIG. 5B). There was a significant 12-fold increase in COX-2 mRNA levels in IL-1α/OSM-stimulated explants relative to untreated cartilage ($p<0.0001$), which was reduced by approximately 75% when co-treated with *B. frereana* ($p=0.0001$).

Epi-Lupeol is the Major Constituent of *B. frereana*.

Figure 6:
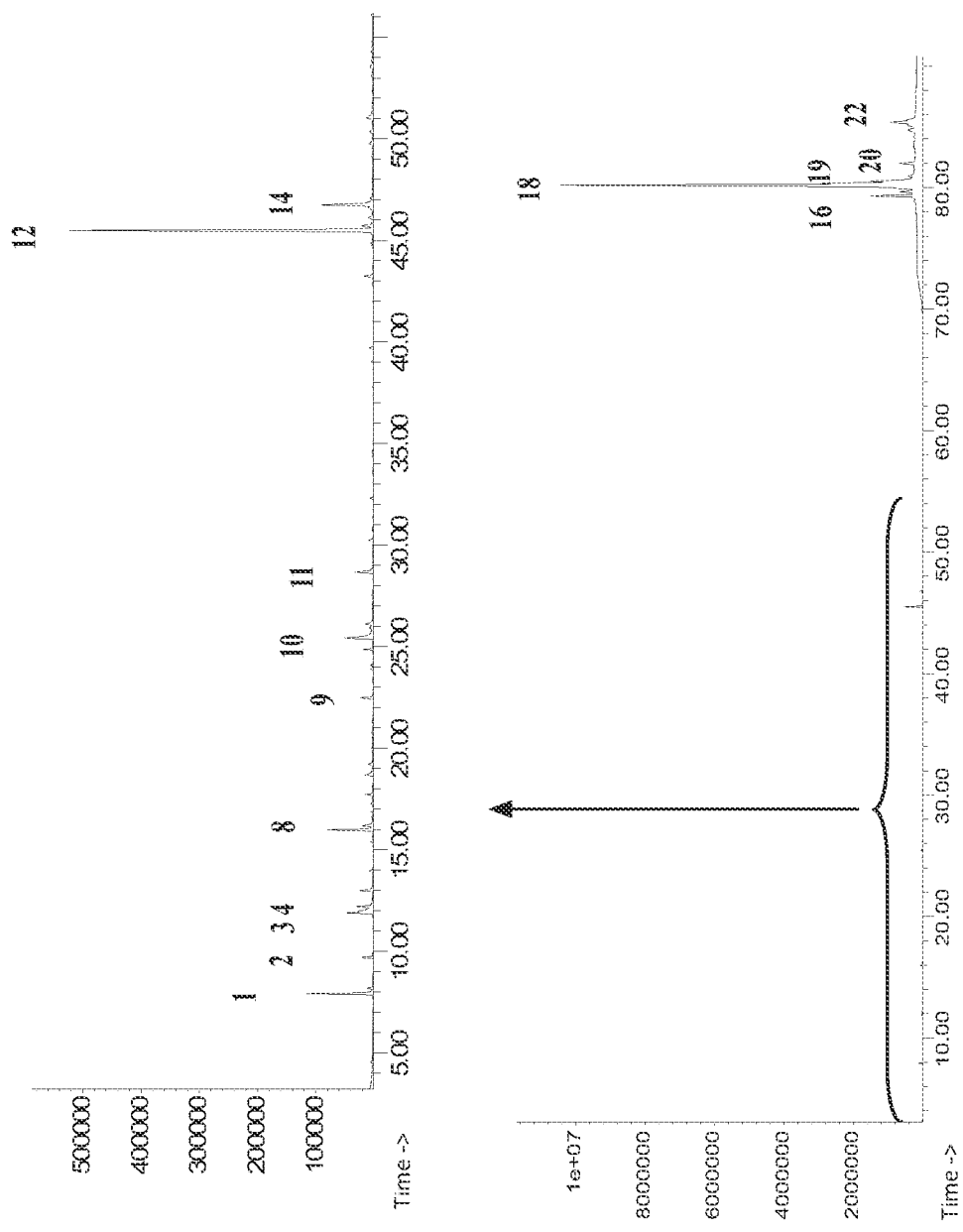

Approximately 81% of the components present in the ethanol extract of *B. frereana* were identified using GC-MS as indicated (FIG. 6). The major component identified, and accounting for 59.3% of the *B. frereana* extract was epi-lupeol (FIG. 6B). Other minor components identified in the ethanolic *B. frereana* extract were β-amyrin (6.35%), Lupeol acetate (3.10%), α-amyrin (2.38%), α-phellandrene dimer 3 (1.10%), α-phellandrene dimer 5 (0.24%), α-thujene (0.34%) and α-phellandrene (0.24%).

*B. frereana* Inhibits Acetylcholinesterase

The extracts of *B. frereana*, after spraying with the enzyme, substrate and detection reagent were found to yield bright white spots on the TLC plates a yellow background. They were able to inhibit the activity of acetylcholinesterase at all the concentrations tested (101.6-3.17 mg/ml). The reference standard galanthamine hydrobromide (1 mM), a known inhibitor of AChE, also gave a bright white spot on the baseline of the TLC plate. No white spots, corresponding to false positives, were observed for the control TLC plate.

*B. frereana* Kills Cancer Cells

Concentrations of the *B. frereana* extract at 800 pg/ml or greater resulted in a decrease in formazan absorbance, indicating a reduction in mitochondrial activity and a reduction in cell number. This decrease in cell number could have occurred if the active components of the *Boswellia* extract were to cause cell cycle arrest (cytostasis). Prolonged cell cycle arrest in a phase other than G0 is intolerable to the cell and will ultimately result in indirect cellular damage and cell death. The cytotoxic components of the *B. frereana* extract may, therefore, be behaving as an apoptotic inducer and an enhancer of cell death towards the MCF-7 human cancer cells.

DISCUSSION

In the present study, we utilised an in vitro model of cartilage degeneration (29, 30) to determine whether the little known *Boswellia* species—*B. frereana* had any anti-inflammatory efficacy, and therefore could be exploited as an alternative therapy for treating a variety of inflammatory disorders. Cartilage explants were treated with 5 ng/ml IL-1α and 10 ng/ml OSM over a 28-day period, in the presence or absence of 100 μg/ml *B. frereana*. There was no evidence of either IL-1/OSM or *B. frereana*-induced cytotoxicity over the 28 day culture period. In this in vitro model, neither the cytokines nor the *B. frereana* had any discernable effect on the amount of sGAG or collagen retained in the explants. However, there was a significant increase in the amount of both sGAG and collagen released from the explants after IL-1α/OSM stimulation for 3 and 21-28 days, respectively, which is in agreement with previous reports (41, 42). In the presence of IL-1α/OSM approximately 50% of the sGAG content was released into the media over the 28 day period therefore it is slightly surprising that the amount of sGAG in the tissue does not reflect this. We surmise that in the presence of the cytokines, the tissue is continually synthesising new sGAG to replace that which is lost (43). Detection of sGAG and collagen in the media mainly represents degradation and release of ECM components from the tissue. Interestingly, *B. frereana* was only able to rescue IL-1α/OSM-mediated collagen degradation. Over the 28 day period, *B. frereana* had no effect on the amount of sGAG released into the media after cytokine stimulation; this would suggest that a different mechanism of action must exist between the collagen and sGAG to explain the differential inhibition observed.

Key mediators of collagen breakdown include MMPs 9 and 13 (44). Increased levels of active MMP 9 have been observed in pathological articular cartilage (1, 3-6). To ascertain whether the observed increase in collagen release by IL-1α/OSM and subsequent modulation by *B. frereana*, represented a catabolic phenotype, the expression and activation status of pro-MMP 9 was analysed. Over the 28 days, both pro-MMP 9 synthesis and its activation increased substantially in cytokine-stimulated explants, which may have contributed to the significant release of collagen at days 21-28, as has been previously reported (44). *B. frereana* inhibited IL-1α/OSM-mediated synthesis and activation of pro-MMP 9 returning expression to basal levels. [IL-1α/OSM did not have a significant effect on pro-MMP 2 expression, although levels of active MMP 2 appeared to increase. After 28 days, *B. frereana* also inhibited activation of pro-MMP 2]. Our data suggests that the reduction in IL-1α/OSM-induced expression of pro-MMP 9 in explants treated with *B. frereana* may arise from the transcriptional inhibition of MMP 9 that we observed.

MMP 9 synthesis is modulated by a variety of pro-inflammatory molecules including NO and COX-2 (45), and it is well established that both NO and COX-2 are involved in cartilage degradation (43, 46). Nitrite, the stable end product of NO, was significantly elevated in cartilage explants stimulated with IL-1α/OSM over the entire culture period, whilst in the presence of *B. frereana*, cytokine-induced NO production was significantly inhibited. We hypothesise that the vast increase in pro-MMP 9 synthesis and activation can, in part, be attributed to NO levels, and that the action of *B. frereana* in inhibiting NO production prevented the downstream synthesis and/or activation of MMP 9. Joint inflammation in OA also increases circulating levels of COX-2—the rate-limiting enzyme in $PGE_2$ synthesis, which causes an increased synthesis of $PGE_2$. A previous study indicated a link between NO and COX-2 expression in a canine model of experimental OA (45). The combination of IL-1α with OSM significantly elevated $PGE_2$ synthesis to approximately 80-fold that observed in the untreated cartilage explants, consistent with previous studies (37, 47). Using the IL-1α/OSM combination, *B. frereana* reduced $PGE_2$ levels although this did not return to basal levels.

To further understand the mechanism of *B. frereana* action in this in vitro inflammatory model of cartilage degradation, we quantified the amount of gene transcripts for iNOS, $PGE_2$ synthase and COX-2 using qPCR. All were observed to increase significantly in the explants treated with IL-1α/OSM, and in the combined presence of *B. frereana*, levels of gene transcription were significantly reduced; however, they did not return to the basal levels observed in untreated explants. Our data would suggest that the inhibitory action of *B. frereana* on NO and $PGE_2$ synthesis is controlled at the transcriptional level.

Although several studies have been performed on *B. serrata*, and its pharmacologically active components have been identified as predominantly α- and β-boswellic acids (24), little is known about the bioactive ingredients of *B. frereana* excepting that it is reported to differ from the other species (48). Using gas chromatography in conjunction with mass spectrometry, we have identified the primary constituents of *B. frereana*, of which epi-lupeol accounts for almost 60% of the extract. Although *B. frereana* has the geneology of the *Boswellia* species, it is devoid of the active components such as boswellic acid, that are characteristic of the other family members, as has previously been alluded to (48). Epi-lupeol is a pentacyclic triterpene; it's isomer lupeol is a naturally occurring triterpene found in various fruits and vegetables including olives, strawberries and fig plants (49). Interestingly, and of potential importance in understanding the mechanisms of *B. frereana* action in our study, is the biochemical properties of lupeol. Lupeol has been shown to have wide-ranging pharamacological properties including anti-inflammatory and anti-arthritic activity in vitro and in vivo (50, 51). Oral administration of lupeol to a rat model of antigen-induced arthritis led to a 39% reduction in paw swelling, and a reduction in the amount of hydroxyproline and sGAGs in the urine indicating that lupeol could ameliorate the symptoms of inflammation (51). Lupeol administered topically to a murine model of inflammation induced by 12-O-tetradecanoyl-phorbol ester suppressed ear edema, due to a significant reduction in $PGE_2$ and a weaker inhibition of nitrite release (50). Our observations support this in vivo data although we saw greater efficacy against nitrite production with respect to $PGE_2$ levels, however, this may reflect the fact that the active component of *B. frereana* is epi-lupeol and not lupeol. Topical administration of lupeol to a mouse skin tumourigenesis model significantly inhibited skin edema and hyperplasia in conjunction with decreased expression of COX-2 and NO synthase (52), agreeing with the efficacy of epi-lupeol in our in vitro study. The reduction in COX-2 and NO synthase was attributed to an inhibition of NF-κB activation. The nuclear transcription factor NF-κB is a key player in the development and progression of chronic inflammatory diseases including rheumatoid arthritis (53). The anti-inflammatory properties of *B. serrata* involve the regulation of NF-κB activation, as demonstrated in a recent study using a mouse model of atherosclerosis (54). However, although *B. serrata* is known to inhibit 5-lipoxygenase function (25), lupeol was shown to have no effect on lipoxygenase products (50), therefore lupeol is not likely to affect the 5-lipoxygenase pathway.

Additionally extract of *B. frereana* was able to inhibit acetylcholinesterase activity and kill a well known model of cancer i.e. breast cancer cell line MCF-7.

To conclude, this is the first report detailing the anti-inflammatory efficacy of *B. frereana* such as in articular cartilage. Our novel data demonstrates that the treatment of IL-1α/OSM stimulated cartilage explants with *B. frereana* confers some protection against degeneration of the tissue by inhibiting the breakdown of the collagenous matrix, through the inhibition of MMP 9 expression and activation, and significant reduction in the expression of inflammatory mediators including NO, $PGE_2$ and COX-2. It follows that *B. frereana* can therefore be exploited as a medicament to treat MMP 9 mediated disorders or conditions where there is a need for a significant reduction in the expression of inflammatory mediators including NO, $PGE_2$ and COX-2. *B. frereana*, which is non-toxic and particularly efficacious for $PGE_2$ regulation may offer an additional perspective for the therapeutic action of this naturally occurring compound. Moreover, *B. frereana* may confer some protection against neurological disorders characterised by increased acetylcholinesterase activity or where it is desirable to block this activity. Further, *B. frereana* has application in the destruction of cancer cells.

Example 2

Development of animal models of IBD has contributed to the understanding and discovery of therapies for IBD. We have previously established the dextran sulfate (DSS) and the trinitrobenzene sulfonic acid (TNBS) colitis rodent models in our laboratory and in a collaborative effort have demonstrated that the severity of weight loss, colon histopathology and endoscopy scores corresponded to the degree of changes in proinflammatory cytokines and chemokines that preferentially attract infiltration of neutrophils and matrix metalloproteinases. The IBD rodent model has also been used to validate a computational approach to identify potential new drug therapies for IBD.

The effect of *Boswellia frereana* in the treatment of an animal model of IBD, specifically, DSS induced colitis, was explored.

Animals

Sixty-five (65) male C57Bl/6 mice with average starting body weight (±SD) of 23.25±1.34 g were obtained from Charles River Laboratories (Wilmington, Mass.). Mice were acclimatized for a minimum of 3 days prior to study commencement. During this period, the animals were observed daily in order to reject animals that presented in poor condition.

Housing

The study was performed in animal rooms provided with HEPA filtered air at a temperature of 70±5° F. and 50%±20% relative humidity. Animal rooms were set to maintain a minimum of 12 to 15 air changes per hour. The room was on an automatic timer for a light/dark cycle of 12 hours on and 12 hours off with no twilight. Sterile Bed-O-Cobs® or equivalent bedding was used. Bedding was changed a minimum of once per week. Cages, tops, and water bottles were washed with a commercial detergent and allowed to air dry. A commercial disinfectant was used to disinfect surfaces and materials introduced into the hood. Floors were swept daily and mopped a minimum of twice weekly with a commercial detergent. Walls and cage racks were sponged a minimum of once per month with a dilute bleach solution. A cage card or label with the appropriate information necessary to identify the study, dose, animal number, and treatment group was used to mark all cages. The temperature and relative humidity was recorded during the study, and the records retained.

Diet

Animals were fed with a sterile Purina Labdiet® 5053 rodent diet and sterilized water was provided ad libitum.

Animal Randomization and Allocations

Mice were randomized into five (5) groups of ten (10) animals and one (1) group of fifteen (15) animals prior to the start of the study. Each animal was identified by an ear punch corresponding to an individual number. A cage card was used to identify each cage and was marked with the study number (INH-01), treatment group number, and animal numbers.

Colitis Induction

Colitis was induced by administration of 3% w/v DSS (MP Biomedicals; Cat #10156) in the drinking water on Days 0 to 5. DSS solution was replaced with a freshly prepared solution on Day 3 and any of the remaining original DSS solution was discarded.

Test Article/Vehicle Preparation

*Boswellia* extract (Lot # R14-038 Batch2 4/15/14) in the specified concentrations was formulated in Corn Oil fresh daily, protected from light, and stored at room temperature. Briefly, *Boswellia* extract was weighed and placed in a small Eppendorf tube. Corn oil was added to make the highest concentration of extract (200 mg/kg). After homogenizing the mixture mechanically, serial dilutions were performed to make the remaining concentrations of *Boswellia* extract. It was delivered via oral Biomodels Study INH-01 Biomodels, LLC/Confidential gavage (p.o.) at a dosing volume of 0.1 mL/20 g body weight (5 mL/kg). Disposition of unused dosing mixture was performed per Biomodels SOP.

Statistical Analyses

Statistical differences between a test group and the vehicle control were determined using one-way ANOVA followed by post-hoc analysis using the Holm-Sidak's multiple comparison test (Graphpad Prism 6.01, Graphpad Software, La Jolla, Calif.).

Experimental Design

In this study, colitis was induced in 55 mice by exposure to 3% DSS-treated drinking water from Day 0 to Day 5. Animals were dosed via oral gavage (p.o.) with test article or corn oil vehicle once a day (q.d.) from Day −2 to 12, as indicated in Table 8. All animals were weighed daily and assessed visually for the presence of Diarrhoea and/or bloody stool at the time of dosing. Video endoscopy was performed on days 7, 10 and 12. At these time points, colitis severity was assessed in all animals using video endoscopy, where images were taken and colitis severity was scored by an observer blind to treatment group designation. Additionally, an image was captured from each animal at the most severe region of disease identified during endoscopy. Following endoscopy on Day 12, all remaining animals from each treatment group were sacrificed.

Upon sacrifice, the colon was excised, the contents removed, and its length and weight measured. The colon was then trimmed to a length of 5 cm and divided into three pieces. The distal 2 cm and proximal 2 cm portion were placed in formalin, for subsequent histological evaluation, while the middle 1 cm portion was weighed and then snap frozen for subsequent biomarker evaluation. Blood was collected and plasma samples were prepared. The details of the study design and group assignment are shown in Table 8.

Outcome Evaluation

Study endpoints were endoscopy colitis score, body weight change, survival, blood for plasma preparation, colon length, colon weight, and colon histology. The presence of diarrhoea and/or the presence of blood in the stool were assessed via visual assessment at the time of dosing.

Survival and Weight Change Data

Animal deaths were evaluated during the course of the study. In this colitis model, animal deaths are commonly attributable to severe weight loss due to severe colitis, toxicity of the experimental compound, or perforation of the colon during endoscopy. Since weight change is a secondary method to examine potential toxicities of experimental treatments, animals were weighed daily throughout the study.

Colitis Evaluation: Endoscopy

Endoscopy was performed in a blinded fashion using a small animal endoscope (Karl Storz Endoskope, Germany). To evaluate colitis severity, animals were anesthetized with isoflurane and subjected to video endoscopy of the lower colon. Colitis was scored visually on a 5 point scale that ranges from 0 for normal, to 4 for severe ulceration. In descriptive terms, this scale is defined as depicted in Table 9. Each mouse was assigned a single score that corresponded to the most severe damage observed throughout the entire length of the colon.

Sacrifice-Endpoints

Upon sacrifice with CO2 inhalation, the colon was excised, the contents removed and collected, and its length and weight measured. The colon was then trimmed to a length of 5 cm and divided into three pieces. The distal 2 cm and proximal 2 cm portion were placed in formalin, for subsequent histological evaluation, while the middle 1 cm portion was weighed and snap frozen for subsequent biomarker evaluation. Blood was collected and plasma samples prepared.

Colitis Scoring

A board certified veterinary pathologist with particular expertise in GI pathology evaluated H&E stained colon sections in a blinded fashion. Each section was assessed for morphological changes/injury to the epithelium, connective tissue, and submucosa using a 5 point scale, in which 0=normal colon; score of 1=minimal inflammation, edema, or necrosis; score of 2=mild inflammation, edema, or necrosis; score of 3=moderate inflammation, edema, or necrosis; and score of 4=marked inflammation, edema, or necrosis. Photomicrographs were taken to document findings.

ELISAs

ELISAs were performed for the biomarkers listed below by using commercially available kits and following the manufacturer instructions/protocols: IL-1β (R&D Systems, # MLB00C); TNF-α (R&D Systems, # MTA00B); COX-2 (R&D Systems, # DYC4198-2); MMP-9 (R&D Systems, # MMPT90); Nitric Oxide (Abcam, # ab5328); IFN-γ (R&D Systems, # MIF00); and IL-2 (R&D Systems, # D2050).

Results

Survival

There were three (3) unanticipated animal deaths during this study. One animal in Group 5 was found dead on Day 9. In Group 6, one animal was sacrificed on Day 7 due to perforation of the colon during endoscopy and one animal was sacrificed on Day 11 due to moribund state and excessive weight loss.

Weight Change

The mean daily percent weight change for all treatment groups is shown in FIG. 13. Animals started losing weight on Day 1. Animals in Groups 2-6 exhibited peak mean weight loss of −19.66±1.38%, −10.66±1.26%, −13.28±1.88%, −19.06±2.14%, and −15.60±2.05%, respectively, on Day 9. Compared to the untreated control group without DSS, all of the groups treated with DSS exhibited significant weight loss (p<0.0001). In comparison to the Vehicle Control Group (Group 2), animals treated with 25 mg/kg (Group 3), 50 mg/kg (Group 4), and 200 mg/kg Boswellia Extract (Group 6) had significantly less weight loss (p<0.01 for Groups 3 and 6, p<0.05 for Group 4) as determined by evaluating the Area-Under-the-Curve (AUC) for body weight change and utilizing one-way ANOVA with Holm-Sidak's Multiple Comparisons post-hoc test (FIG. 14). On the last day of the study (Day 12), the average body weight of animals (in grams±SEM) in Groups 1-6 was as follows: 25.20±0.67 (Group 1), 19.41±0.61 (Group 2), 22.47±0.42 (Group 3), 20.95±0.37 (Group 4), 20.03±0.75 (Group 5), and 21.29±0.55 (Group 6). Evaluation using unpaired student's t-test revealed that, in comparison to the Untreated Control Group (Group 1), animals in all other groups had significantly less weight (p<0.01-p<0.0001). In comparison to the Vehicle Control Group (Group 2), only animals in Group 3 (p<0.01) had significantly more weight. No other groups had statistically significant differences in weight on Day 12 in comparison to Group 2.

Endoscopy—Colitis Scores

All animals underwent video endoscopy on Days 7, 10, and 12 to assess the severity of colitis in each treatment group. The mean colitis scores for all treatment groups are shown in FIG. 15 (Day 7), FIG. 16 (Day 10), and FIG. 17 (Day 12). Treatment with DSS on Days 0 to 5 successfully induced colitis as determined by video endoscopy on Days 7, 10, and 12 in all the DSS-treated groups in comparison to the Untreated Control Group (Group 1). There were no statistically significant differences in mean endoscopy colitis scores between the Boswellia Extract treatment groups and the Vehicle Control Group on Days 7 and 10. On Day 12, animals treated with 25 mg/kg Boswellia Extract (Group 3) had a statistically significant (p<0.01) reduction in mean endoscopy colitis scores in comparison to the Vehicle Control Group (Group 2). Representative endoscopic images of the treatment groups on Days 7, 10, and 12 are shown in FIGS. 18-23.

Colon Weight

Animals were sacrificed on Day 12 and their colons were removed and weighed. The mean colon weights for all treatment groups are shown in FIG. 24. There were no significant differences in mean colon weight among any of the groups in comparison to the Vehicle Control Group (Group 2).

Colon Length

Animals were sacrificed on Day 12 and their colons were removed and their lengths measured. The mean colon length for all treatment groups are shown in FIG. 25. In comparison to the Vehicle Control Group, animals in the Naïve Control Group had statistically significant longer colons (p<0.0001). Furthermore, animals treated with 25 mg/kg and 50 mg/kg (Group 3 and Group 4, respectively) also had significantly longer colon lengths than the Vehicle Control Group (p<0.05 for both).

Diarrhoea & Bloody Stool

Diarrhoea was first observed on Day 6 from animals in the Vehicle Control Group and from animals treated with 100 mg/kg Boswellia Extract. On Day 7, Diarrhoea was observed in at least one animal in each DSS-treated group. Diarrhoea peaked between Days 8-10 for most DSS-treated groups. Generally, the incidence of Diarrhoea was lower in animals treated with Boswellia Extract in comparison to animals treated with Vehicle (Table 10). The incidence of bloody stool was less common than the incidence of Diarrhoea (Table 11).

ELISAs

Figure 26B:
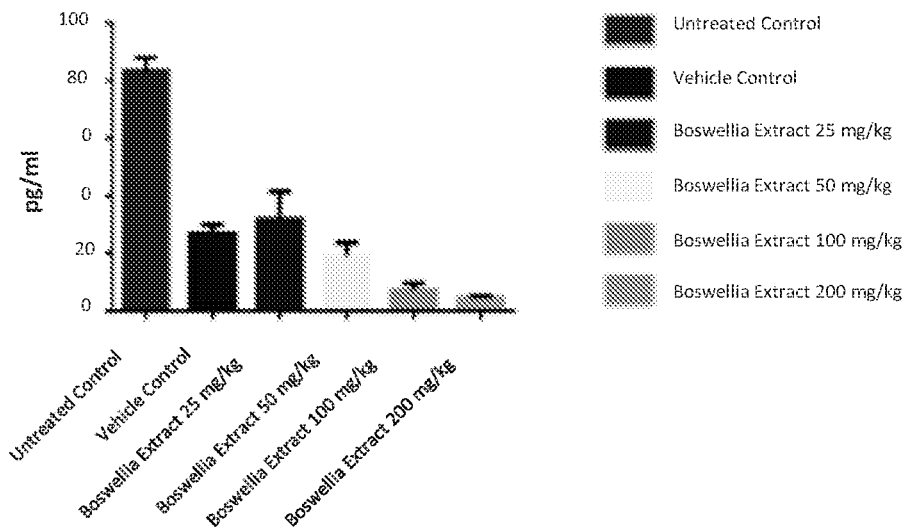

ELISAs were performed by using commercially available kits and following the manufacturer instructions/protocols for the following markers: TNFα, IL-1β, MMP9, Nitric Oxide, IL-2, and IFN-γ. The results are illustrated within FIG. 26. Briefly, induction of colitis via DSS exposure increased TNFα, IL-1b and MMP9 levels and decreased Nitric Oxide, IL-2 and IFN-Gamma levels. Treatment with Boswellia extract at the 25 mg/kg concentration was most effective at moderating levels for TNF-α, IL-1b, and MMP9 and a higher concentration was most effective at moderating the levels of IL-2. Boswellia extract was less effective at moderating the levels of Nitric Oxide, and IFN-gamma.

Discussion

1. There were three (3) unanticipated animal deaths during this study. One animal in Group 5 was found dead on Day 9. In Group 6, one animal was sacrificed on Day 7 due to perforation of the colon during endoscopy and one animal was sacrificed on Day 11 due to moribund state and excessive weight loss.

2. Animals started losing weight on Day 1. Animals in Groups 2-6 exhibited peak mean weight loss of −19.66±1.38%, −10.66±1.26%, −13.28±1.88%, −19.06±2.14%, and −15.60±2.05%, respectively, on Day 9. Compared to the untreated control group without DSS, all of the groups treated with DSS exhibited significant weight loss (p<0.0001). In comparison to the Vehicle Control Group (Group 2), animals treated with 25 mg/kg (Group 3), 50 mg/kg (Group 4), and 200 mg/kg Boswellia Extract (Group 6) had significantly less weight loss (p<0.01 for Groups 3 and 6, p<0.05 for Group 4). On the last day of the study (Day 12), the average body weight of animals (in grams±SEM) in Groups 1-6 was as follows: 25.20±0.67 (Group 1), 19.41±0.61 (Group 2), 22.47±0.42 (Group 3), 20.95±0.37 (Group 4), 20.03±0.75 (Group 5), and 21.29±0.55 (Group 6). Evaluation using unpaired student's t-test revealed that, in comparison to the Untreated Control Group (Group 1), animals in all other groups had significantly less weight (p<0.01-p<0.0001). In comparison to the Vehicle Control Group (Group 2), only animals in Group 3 (p<0.01) had significantly more weight. No other groups had statistically significant differences in weight on Day 12 in comparison to Group 2.

3. Treatment with DSS on Days 0 to 5 successfully induced colitis as determined by video endoscopy on Days 7, 10, and 12 in all the DSS-treated groups in comparison to the Untreated Control Group (Group 1). There were no statistically significant differences in mean endoscopy colitis scores between the *Boswellia* Extract treatment groups and the Vehicle Control Group on Days 7 and 10. On Day 12, animals treated with 25 mg/kg *Boswellia* Extract (Group 3) had a statistically significant reduction in mean endoscopy colitis scores in comparison to the Vehicle Control Group (Group 2).

4. There were no significant differences in mean colon weight among any of the groups in comparison to the Vehicle Control Group (Group 2)

5. In comparison to the Vehicle Control Group, animals in the Naïve Control Group had statistically significant longer colons (p<0.0001). Furthermore, animals treated with 25 mg/kg and 50 mg/kg (Group 3 and Group 4, respectively) also had significantly longer colon lengths than the Vehicle Control Group (p<0.05 for both).

6. Diarrhoea was first observed on Day 6 from animals in the Vehicle Control Group and from animals treated with 100 mg/kg *Boswellia* Extract. On Day 7, Diarrhoea was observed in at least one animal in each DSS-treated group. Diarrhoea peaked between Days 8-10 for most DSS-treated groups. Generally, the incidence of Diarrhoea was lower in animals treated with *Boswellia* Extract in comparison to animals treated with Vehicle. The incidence of bloody stool was less common than the incidence of Diarrhoea (Table 11).

7. Treatment with *Boswellia* Extract at doses ranging from 25 mg/kg to 200 mg/kg reduced inflammation scores, edema scores, necrosis scores and sum scores compared to the vehicle control group, but the treatment differences were not significant for any parameter.

8. Induction of colitis via DSS exposure increased TNFα, IL-1b and MMP9 levels and decreased Nitric Oxide, IL-2 and IFN-Gamma levels. Treatment with *Boswellia* extract at the 25 mg/kg concentration was most effective at moderating levels for TNF-α, IL-1b, and MMP9 and a higher concentration was most effective at moderating the levels of IL-2. *Boswellia* extract was less effective at moderating the levels of Nitric Oxide, and IFN-gamma.

REFERENCES

1. Davidson R K, Waters J G, Kevorkian L, Darrah C, Cooper A, Donell S T, et al. Expression profiling of metalloproteinases and their inhibitors in synovium and cartilage. Arthritis Res Ther. 2006; 8(4):R124.
2. Bayliss M T, Hutton S, Hayward J, Maciewicz R A. Distribution of aggrecanase (ADAMts 4/5) cleavage products in normal and osteoarthritic human articular cartilage: the influence of age, topography and zone of tissue. Osteoarthritis Cartilage. 2001 August; 9(6):553-60.
3. Cawston T E, Wilson A J. Understanding the role of tissue degrading enzymes and their inhibitors in development and disease. Best Pract Res Clin Rheumatol. 2006 October; 20(5):983-1002.
4. Dean D D, Martel-Pelletier J, Pelletier J P, Howell D S, Woessner J F, Jr. Evidence for metalloproteinase and metalloproteinase inhibitor imbalance in human osteoarthritic cartilage. J Clin Invest. 1989 August; 84(2):678-85.
5. Mohtai M, Smith R L, Schurman D J, Tsuji Y, Torti F M, Hutchinson N I, et al. Expression of 92-kD type IV collagenase/gelatinase (gelatinase B) in osteoarthritic cartilage and its induction in normal human articular cartilage by interleukin 1. J Clin Invest. 1993 July; 92(1):179-85.
6. Soder S, Roach H I, Oehler S, Bau B, Haag J, Aigner T. MMP-9/gelatinase B is a gene product of human adult articular chondrocytes and increased in osteoarthritic cartilage. Clin Exp Rheumatol. 2006 May-June; 24(3):302-4.
7. Struglics A, Larsson S, Pratta M A, Kumar S, Lark M W, Lohmander L S. Human osteoarthritis synovial fluid and joint cartilage contain both aggrecanase- and matrix metalloproteinase-generated aggrecan fragments. Osteoarthritis Cartilage. 2006 February; 14(2):101-13.
8. Plaas A, Osborn B, Yoshihara Y, Bai Y, Bloom T, Nelson F, et al. Aggrecanolysis in human osteoarthritis: confocal localization and biochemical characterization of ADAMTS5-hyaluronan complexes in articular cartilages. Osteoarthritis Cartilage. 2007 July; 15(7):719-34.
9. Le Pen C, Reygrobellet C, Gerentes I. Financial cost of osteoarthritis in France. The "COART" France study. Joint Bone Spine. 2005 December; 72(6):567-70.
10. Lawrence R C, Felson D T, Helmick C G, Arnold L M, Choi H, Deyo R A, et al. Estimates of the prevalence of arthritis and other rheumatic conditions in the United States. Part II. Arthritis Rheum. 2008 January; 58(1):26-35.
11. Berenbaum F. New horizons and perspectives in the treatment of osteoarthritis. Arthritis Res Ther. 2008; 10 Suppl 2:S1.
12. Schulze-Tanzil G, Mobasheri A, Sendzik J, John T, Shakibaei M. Effects of curcumin (diferuloylmethane) on nuclear factor kappaB signaling in interleukin-1beta-stimulated chondrocytes. Ann N Y Acad Sci. 2004 December; 1030:578-86.
13. Shakibaei M, Csaki C, Nebrich S, Mobasheri A. Resveratrol suppresses interleukin-1beta-induced inflammatory signaling and apoptosis in human articular chondrocytes: potential for use as a novel nutraceutical for the treatment of osteoarthritis. Biochem Pharmacol. 2008 Dec. 1; 76(11):1426-39.
14. Adcocks C, Collin P, Buttle D J. Catechins from green tea (*Camellia sinensis*) inhibit bovine and human cartilage proteoglycan and type II collagen degradation in vitro. J Nutr. 2002 March; 132(3):341-6.
15. Ernst E. Frankincense: systematic review. Bmj. 2008; 337:a2813.
16. Ammon H P. Boswellic acids in chronic inflammatory diseases. Planta Med. 2006 October; 72(12):1100-16.
17. Madisch A, Miehlke S, Eichele O, Mrwa J, Bethke B, Kuhlisch E, et al. *Boswellia serrata* extract for the treatment of collagenous colitis. A double-blind, randomized, placebo-controlled, multicenter trial. Int J Colorectal Dis. 2007 December; 22(12):1445-51.
18. Gerhardt H, Seifert F, Buvari P, Vogelsang H, Repges R. [Therapy of active Crohn disease with *Boswellia serrata* extract H15]. Z Gastroenterol. 2001 January; 39(1):11-7.
19. Sander O, Herborn G, Rau R. [Is H15 (resin extract of *Boswellia serrata*, "incense") a useful supplement to established drug therapy of chronic polyarthritis? Results of a double-blind pilot study]. Z Rheumatol. 1998 February; 57(1):11-6.
20. Singh S, Khajuria A, Taneja S C, Johri R K, Singh J, Qazi G N. Boswellic acids: A leukotriene inhibitor also effective through topical application in inflammatory disorders. Phytomedicine. 2008 June; 15(6-7):400-7.

21. Kimmatkar N, Thawani V, Hingorani L, Khiyani R. Efficacy and tolerability of *Boswellia serrata* extract in treatment of osteoarthritis of knee—a randomized double blind placebo controlled trial. Phytomedicine. 2003 January; 10(1):3-7.

22. Sontakke S, Thawani V, Pimpalkhute P, Kabra P, Babhulkar S, Hingorani H. Open, randomised, controlled clinical trial of *Boswellia serrata* extract as compared to valdercoxib in osteoarthritis of knee. Indian Journal of Pharmacology. 2007; 39:27-9.

23. Sengupta K, Alluri K V, Satish A R, Mishra S, Golakoti T, Sarma K V, et al. A double blind, randomized, placebo controlled study of the efficacy and safety of 5-Loxin for treatment of osteoarthritis of the knee. Arthritis Res Ther. 2008; 10(4):R85.

24. Pardhy R S, Bhattacharya S C. Boswellic acid, acetyl-boswellic acid and 11-keto-boswellic acid, four pentacyclic triterpenic acids from the resin of *Boswellia serrata*. Indian Journal of Chemistry. 1978; 16B:176-8.

25. Safayhi H, Mack T, Sabieraj J, Anazodo M I, Subramanian L R, Ammon H P. Boswellic acids: novel, specific, nonredox inhibitors of 5-lipoxygenase. J Pharmacol Exp Ther. 1992 June; 261(3):1143-6.

26. Siemoneit U, Hofmann B, Kather N, Lamkemeyer T, Madlung J, Franke L, et al. Identification and functional analysis of cyclooxygenase-1 as a molecular target of boswellic acids. Biochem Pharmacol. 2008 Jan. 15; 75(2):503-13.

27. Zhao W, Entschladen F, Liu H, Niggemann B, Fang Q, Zaenker K S, et al. Boswellic acid acetate induces differentiation and apoptosis in highly metastatic melanoma and fibrosarcoma cells. Cancer Detect Prev. 2003; 27(1):67-75.

28. Frank A, Unger M. Analysis of frankincense from various *Boswellia* species with inhibitory activity on human drug metabolising cytochrome P450 enzymes using liquid chromatography mass spectrometry after automated on-line extraction. J Chromatogr A. 2006 Apr. 21; 1112(1-2):255-62.

29. Rowan A D, Koshy P J, Shingleton W D, Degnan B A, Heath J K, Vernallis A B, et al. Synergistic effects of glycoprotein 130 binding cytokines in combination with interleukin-1 on cartilage collagen breakdown. Arthritis Rheum. 2001 July; 44(7):1620-32.

30. Barksby H E, Hui W, Wappler I, Peters H H, Milner J M, Richards C D, et al. Interleukin-1 in combination with oncostatin M up-regulates multiple genes in chondrocytes: implications for cartilage destruction and repair. Arthritis Rheum. 2006 February; 54(2):540-50.

31. Blain E J, Gilbert S J, Hayes A J, Duance V C. Disassembly of the vimentin cytoskeleton disrupts articular cartilage chondrocyte homeostasis. Matrix Biol. 2006 September; 25(7):398-408.

32. Little C B, Flannery C R, Hughes C E, Mort J S, Roughley P J, Dent C, et al. Aggrecanase versus matrix metalloproteinases in the catabolism of the interglobular domain of aggrecan in vitro. Biochem J. 1999 Nov. 15; 344 Pt 1:61-8.

33. Neuman R E, Logan M A. The determination of hydroxyproline. J Biol Chem. 1950 May; 184(1):299-306.

34. Blain E J, Gilbert S J, Wardale R J, Capper S J, Mason D J, Duance V C. Up-regulation of matrix metalloproteinase expression and activation following cyclical compressive loading of articular cartilage in vitro. Arch Biochem Biophys. 2001 Dec. 1; 396(1):49-55.

35. Blain E J, Mason D J, Duance V C. The effect of cyclical compressive loading on gene expression in articular cartilage. Biorheology. 2003; 40(1-3):111-7.

36. Gilbert S J, Blain E J, Duance V C, Mason D J. Sphingomyelinase decreases type II collagen expression in bovine articular cartilage chondrocytes via the ERK signaling pathway. Arthritis Rheum. 2008 January; 58(1):209-20.

37. Chowdhury T T, Arghandawi S, Brand J, Akanji O O, Bader D L, Salter D M, et al. Dynamic compression counteracts IL-1beta induced inducible nitric oxide synthase and cyclo-oxygenase-2 expression in chondrocyte/agarose constructs. Arthritis Res Ther. 2008; 10(2):R35.

38. Frye S R, Yee A, Eskin S G, Guerra R, Cong X, McIntire L V. cDNA microarray analysis of endothelial cells subjected to cyclic mechanical strain: importance of motion control. Physiol Genomics. 2005 Mar. 21; 21(1):124-30.

39. Livak K J, Schmittgen T D. Analysis of relative gene expression data using real-time quantitative PCR and the 2(-Delta Delta C(T)) Method. Methods. 2001 December; 25(4):402-8.

40. Davies L C, Blain E J, Gilbert S J, Caterson B, Duance V C. The Potential of IGF-1 and TGFbeta1 for Promoting "Adult" Articular Cartilage Repair: An In Vitro Study. Tissue Eng Part A. 2008 Apr. 9.

41. Little C B, Flannery C R, Hughes C E, Goodship A, Caterson B. Cytokine induced metalloproteinase expression and activity does not correlate with focal susceptibility of articular cartilage to degeneration. Osteoarthritis Cartilage. 2005 February; 13(2):162-70.

42. Morgan T G, Rowan A D, Dickinson S C, Jones D, Hollander A P, Deehan D, et al. Human nasal cartilage responds to oncostatin M in combination with interleukin 1 or tumour necrosis factor alpha by the release of collagen fragments via collagenases. Ann Rheum Dis. 2006 February; 65(2): 184-90.

43. Goldring M B, Goldring S R. Osteoarthritis. J Cell Physiol. 2007 December; 213(3):626-34.

44. Milner J M, Rowan A D, Cawston T E, Young D A. Metalloproteinase and inhibitor expression profiling of resorbing cartilage reveals pro-collagenase activation as a critical step for collagenolysis. Arthritis Res Ther. 2006; 8(5):R142.

45. Pelletier J P, Lascau-Coman V, Jovanovic D, Fernandes J C, Manning P, Connor J R, et al. Selective inhibition of inducible nitric oxide synthase in experimental osteoarthritis is associated with reduction in tissue levels of catabolic factors. J Rheumatol. 1999 September; 26(9):2002-14.

46. Lotz M. The role of nitric oxide in articular cartilage damage. Rheum Dis Clin North Am. 1999 May; 25(2):269-82.

47. Morisset S, Patry C, Lora M, de Brum-Fernandes A J. Regulation of cyclooxygenase-2 expression in bovine chondrocytes in culture by interleukin 1alpha, tumor necrosis factor-alpha, glucocorticoids, and 17beta-estradiol. J Rheumatol. 1998 June; 25(6):1146-53.

48. Mathe C, Culioli G, Archier P, Vieillescazes C. Characterization of archaeological frankincense by gas chromatography-mass spectrometry. J Chromatogr A. 2004 Jan. 16; 1023(2):277-85.

49. Chaturvedi P K, Bhui K, Shukla Y. Lupeol: connotations for chemoprevention. Cancer Lett. 2008 May 8; 263(1):1-13.

50. Fernandez M A, de las Heras B, Garcia M D, Saenz M T, Villar A. New insights into the mechanism of action of the anti-inflammatory triterpene lupeol. Journal of Pharmacy and Pharmacology. 2001; 53:1533-9.

51. Geetha T, Varalakshmi P. Effect of lupeol and lupeol linoleate on lysosomal enzymes and collagen in adjuvant-induced arthritis in rats. Mol Cell Biochem. 1999 November; 201(1-2):83-7.

52. Saleem M, Afaq F, Adhami V M, Mukhtar H. Lupeol modulates NF-kappaB and PI3K/Akt pathways and inhibits skin cancer in CD-1 mice. Oncogene. 2004 Jul. 1; 23(30):5203-14.
53. Tak P P, Firestein G S. NF-kappaB: a key role in inflammatory diseases. J Clin Invest. 2001 January; 107 (1):7-11.
54. Cuaz-Perolin C, Billiet L, Bauge E, Copin C, Scott-Algara D, Genze F, et al. Antiinflammatory and anti-atherogenic effects of the NF-kappaB inhibitor acetyl-11-keto-beta-boswellic acid in LPS-challenged ApoE−/− mice. Arterioscler Thromb Vasc Biol. 2008 February; 28(2):272-7.
55. Sen, K. A., Das, I. L. A., Banerji, N. and Vignon, R. M. (1992). Isolation and structure of a 4-O-methyl-glucuronoarabinogalactan from *Boswellia serrata*. *Carbohydrate Research*, 223, 321-327.
56. Rhee, I. K., van de Meent, M., Ingkanina, K. and Verpoorte, R. (2001). Screening for acetylcholinesterase inhibitors from Amaryllidaceae using silica gel thin layer chromatography in combination with bioactivity staining. Journal of chromatography A, 915, 217-223.
57. Ellman, L., Courtney, V. Andresjr, V. and Featherstone, R. M. (1961). A new and rapid Colorimetric determination of acetylcholinesterase activity. Biochem. Pharmacol., 7, 88-95.
58. LEvenson A S and Jordan C V. (1997). The First Hormone-responsive Breast Cancer Cell Line. *Perspectives in Cancer Research*. 57, 3071-3078.
59. Ryan B F and Joiner B L. (1994). *Minitab handbook (third edition)*. Duxbury Press.

TABLE 1

| Gene of Interest | Primer Sequence | Product size (bp) |
|---|---|---|
| iNOS | F 5'-TGTTCAGCTGTGCCTTCAAC-3' (SEQ ID NO 1) R 5'-AAAGCGCAGAACTGAGGGTA-3' (SEQ ID NO 2) | 232 |
| PGE$_2$ synthase | F 5'-GGACGCTCAGAGACATGGAG-3' (SEQ ID NO 3) R 5'-TATGCCACGGTGTGTACCATA-3' (SEQ ID NO 4) | 206 |
| MMP 9 | F 5'-TAGCACGCACGACATCTTTC-3' (SEQ ID NO 5) R 5'-GAAGGTCACGTAGCCCACAT-3' (SEQ ID NO 6) | 121 |

TABLE 2

Resin content of *B. frereana* oleoresin after extraction with hexane (nonpolar solvent) and ethanol (polar solvent).

| Extraction Solvent | Original oleoresin weight (g) | Weight of resin extracted (g) | % Resin[1] (ethanol soluble fraction) | % Gum Residue[2] |
|---|---|---|---|---|
| Hexane | 20.0 | 19.8 | 98.8 | 1.3 |
| Ethanol | 20.0 | 19.9 | 99.3 | 0.7 |

[1]Resin also contains a small amount of essential oil- see table 4 for essential oil content of *B. frereana*.
[2]Calculated by subtracting % resin content from 100.

TABLE 3

Comparison of the gum content of *Boswellia frereana* with related species.

| Boswellia spp. | Country Of Origin | Original oleo-resin weight (g) | Weight of gum (g) (ethanol insoluble fraction) | % Gum (ethanol insoluble fraction) | % Resin (ethanol soluble fraction) |
|---|---|---|---|---|---|
| B. serrata[a] | India | 10.0 | 2.4 | 24.0 | — |
| B. serrata[b] | India | — | — | — | 25-40 |
| B. papyrifera[c] | Ethiopia | 40.2 | 20.7 | 51.4 | 48.6 |
| B. carterii[c] | Somaliland | 40.1 | 22.1 | 55.0 | 45.0 |
| B. carterii[c] | Somaliland | 40.2 | 19.3 | 48.0 | 51.9 |
| B. frereana[c] | Somaliland | 40.1 | 0.7 | 1.7 | 98.3 |
| B. frereana[c] | Somaliland | 40.3 | 0.6 | 1.4 | 98.6 |
| B. frereana[c] | Somaliland | 40.0 | 0.7 | 1.7 | 98.3 |
| B. frereana[c] | Somaliland | 40.0 | 0.5 | 1.2 | 98.8 |

[a]% Gum reported by Sen et al., 1992.
[b]% Resin reported by Natural Remedies PVT Limited
[c]% Resin calculated by subtracting % gum content from 100.

TABLE 4

Summary of the Components of *B. frereana* Oleoresin

| Chemical Constituents of *B. frereana* Oleoresin | % w/w |
|---|---|
| Volatile fraction (Essential) Oil) | 0.9 |
| Alcohol Soluble Fraction (Resin) | 98.3-99.3 |
| Alcohol Insoluble Fraction (Polysaccharide gum) | 0.6-1.6 |

TABLE 5

Essential oil content of *B. frereana* oleoresin extracted by hydro-distillation

| Extraction Solvent | Original oleoresin weight (g) | Weight of essential oil extracted (g) | % Essential oil |
|---|---|---|---|
| Steam | 50.4 | 0.4 | 0.9 |

TABLE 6

Chemical Components Identified In Various Extracts Of *B. frereana* Oleoresin (Essential Oil, Hexane And Ethanol)

| | Fraction isolated (Extraction Method) | | |
|---|---|---|---|
| Chemical Components | Essential Oil (Steam Distillation) % Peak Area | Resin (Hexane) % Peak Area | Resin (Ethanol) % Peak Area |
| α-Thujene | | 0.76 | 0.34 |
| α-Pinene | 9.85 | | |
| Sabinene | | 0.011 | N.D |
| β-Pinene | 2.62 | N.D | N.D |
| α-Phellandrene | Trace | N.D | N.D |
| m-Cymene | 1.62 | 0.118 | 0.074 |
| p-Cymene | 5.49 | N.D | trace |
| Thujol | 5.22 | 0.21 | 0.136 |
| Eucalyptol | 0.91 | 0.18 | 0.135 |
| Thujol | 2.87 | 0.065 | 0.058 |
| trans-2-Caren-4-ol | 1.92 | 0.047 | 0.042 |
| Unknown | 3.89 | N.D | N.D |
| trans-Pinocarveol | 2.51 | N.D | N.D |

TABLE 6-continued

Chemical Components Identified In Various Extracts Of
B. frereana Oleoresin (Essential Oil, Hexane And Ethanol)

| Chemical Components | Essential Oil (Steam Distillation) % Peak Area | Resin (Hexane) % Peak Area | Resin (Ethanol) % Peak Area |
|---|---|---|---|
| (S)-cis-Verbenol | 0.62 | N.D | N.D |
| Thujen-2-ene/Thujone | 3.19 | 0.056 | 0.050 |
| Sabinol | 3.62 | 0.047 | trace |
| Terpinen-4-ol | 6.59 | N.D | N.D |
| p-Cymen-8-ol | 2.67 | N.D | N.D |
| $\alpha$-Terpineol | 1.55 | N.D | N.D |
| Verbenone | 0.94 | N.D | N.D |
| Cuminaldehyde | 0.87 | N.D | N.D |
| Unknown | 3.07 | N.D | N.D |
| Bornyl acetate | 0.54 | N.D | N.D |
| Cuminol | 1.52 | N.D | N.D |
| Carvacrol | 1.53 | N.D | N.D |
| $\beta$-Bourbonene | 2.89 | 0.100 | 0.095 |
| t-Cadinol | 0.37 | N.D | trace |
| $\alpha$-Phellandrene dimer 1 | 0.14 | N.D | trace |
| $\alpha$-Phellandrene dimer 2 | 0.56 | 0.044 | trace |
| $\alpha$-Phellandrene dimer 3 | 11.45 | 1.34 | 1.103 |
| $\alpha$-Phellandrene dimer 4 | 0.42 | 0.057 | 0.042 |
| $\alpha$-Phellandrene dimer 5 | 2.35 | 0.299 | 0.243 |
| Lupeol | N.D | 0.094 | 0.087 |
| $\beta$-Amyrin | N.D | 6.502 | 6.357 |
| $\alpha$-Amyrin | N.D | 2.39 | 2.384 |
| epi-Lupeol | N.D | 60.32 | 59.32 |
| Unknown | N.D | 7.28 | 7.266 |
| Lupeol acetate | N.D | 2.96 | 3.105 |
| % Compounds Identified | 81.79 | 82.88 | 80.85 |

Comparison of the GC-MS Chromatographic Profile of the Essential Oil and Hexane Extract of B. frereana

TABLE 7

LD50 values of MCF-7 cells at 24, 48 and 72 hours incubation.

| MCF-7 | $LD_{50}$ dose (µg/ml) |
|---|---|
| 24 hours | 1630 |
| 48 hours | 1450 |
| 72 hours | 1310 |

TABLE 8

INH-01 Study Design

| Group | Number of Animals | Treatment | Route | Dosing Schedule | D55 Day 0-5 | Video Endoscopy Schedule | Sacrifice Schedule |
|---|---|---|---|---|---|---|---|
| 1 | 10 males | Untreated Control | — | — | — | Day 7, 10 & 12 | Day 12 |
| 2 | 15 males | Vehicle Control (Corn Oil) | P.O. | q.d. Day −2 to 12 | 3% | Day 7, 10 & 12 | Day 12 |
| 3 | 10 males | Boswellia Extract 25 mg/kg | P.O. | q.d. Day −2 to 12 | 3% | Day 7, 10 & 12 | Day 12 |
| 4 | 10 males | Boswellia Extract 50 mg/kg | P.O. | q.d. Day −2 to 12 | 3% | Day 7, 10 & 12 | Day 12 |
| 5 | 10 males | Boswellia Extract 100 mg/kg | P.O. | q.d. Day −2 to 12 | 3% | Day 7, 10 & 12 | Day 12 |
| 6 | 10 males | Boswellia Extract 200 mg/kg | P.O. | q.d. Day −2 to 12 | 3% | Day 7, 10 & 12 | Day 12 |

TABLE 9

Endoscopy Colitis Scoring Scale

| Score | Description: |
|---|---|
| 0 | Normal |
| 1 | Loss of vascularity |
| 2 | Loss of vascularity and friability |
| 3 | Friability and erosions |
| 4 | Ulcerations and bleeding |

TABLE 10

Percent of Mice with Diarrhoea

| Day | Naive Control No-DSS | Vehicle Control + DSS | Boswellia Extract 25 mg/kg | Boswellia Extract 50 mg/kg | Boswellia Extract 100 mg/kg | Boswellia Extract 200 mg/kg |
|---|---|---|---|---|---|---|
| −2 to 5 | 0.00 | 0.00 | 0.00 | 0.00 | 0.00 | 0.00 |
| 6 | 0.00 | 13.33 | 0.00 | 0.00 | 10.00 | 0.00 |
| 7 | 0.00 | 33.33 | 20.00 | 20.00 | 30.00 | 33.33 |
| 8 | 0.00 | 40.00 | 20.00 | 50.00 | 30.00 | 33.33 |
| 9 | 0.00 | 53.33 | 10.00 | 10.00 | 33.33 | 11.11 |
| 10 | 0.00 | 33.33 | 40.00 | 20.00 | 33.33 | 11.11 |
| 11 | 0.00 | 20.00 | 10.00 | 20.00 | 33.33 | 25.00 |
| 12 | 0.00 | 20.00 | 0.00 | 0.00 | 0.00 | 0.00 |

TABLE 11

Percent of Mice with Bloody Stool

| Day | Naive Control No-DSS | Vehicle Control + DSS | Boswellia Extract 25 mg/kg | Boswellia Extract 50 mg/kg | Boswellia Extract 100 mg/kg | Boswellia Extract 200 mg/kg |
|---|---|---|---|---|---|---|
| −2 to 4 | 0.00 | 0.00 | 0.00 | 0.00 | 0.00 | 0.00 |
| 5 | 0.00 | 6.67 | 0.00 | 0.00 | 0.00 | 10.00 |
| 6 | 0.00 | 0.00 | 0.00 | 0.00 | 10.00 | 0.00 |
| 7 | 0.00 | 0.00 | 10.00 | 0.00 | 10.00 | 0.00 |
| 8 | 0.00 | 0.00 | 0.00 | 10.00 | 10.00 | 11.11 |

TABLE 11-continued

Percent of Mice with Bloody Stool

| Day | Naive Control No-DSS | Vehicle Control + DSS | Boswellia Extract 25 mg/kg | Boswellia Extract 50 mg/kg | Boswellia Extract 100 mg/kg | Boswellia Extract 200 mg/kg |
|---|---|---|---|---|---|---|
| 9 | 0.00 | 0.00 | 0.00 | 0.00 | 11.11 | 0.00 |
| 10 | 0.00 | 0.00 | 0.00 | 0.00 | 0.00 | 0.00 |
| 11 | 0.00 | 0.00 | 0.00 | 0.00 | 0.00 | 0.00 |
| 12 | 0.00 | 0.00 | 0.00 | 0.00 | 0.00 | 0.00 |

The invention claimed is:

1. A method of treating a disorder or condition selected from the group consisting of inflammatory bowel disease (IBD), breast cancer, inflammation, and a combination thereof in a patient in need thereof, comprising administering to said patient an effective amount of an alcohol extract of *Boswellia frereana*, wherein said extract comprises epi-lupeol or a salt thereof, and wherein the extract is devoid of boswellic acids.

2. The method of claim 1, wherein said extract comprises one or more of the following: β-amyrin, α-amyrin, α-phellandrene dimers, α-thujene, and α-phellandrene, and isomers or salts thereof.

3. The method of claim 1, wherein said extract comprises one or more of the following: β-amyrin, α-phellandrene dimers, and isomers or salts thereof.

4. The method of claim 1, wherein said extract is a methanol extract.

5. The method of claim 1, wherein said extract is an ethanol extract.

6. A method of treating a disorder or condition selected from the group consisting of inflammatory bowel disease (IBD), breast cancer, inflammation, and a combination thereof in a patient in need thereof, comprising administering to said patient:

a. an effective amount of an alcohol extract of *Boswellia frereana*, wherein said extract comprises epi-lupeol or a salt thereof, and wherein the extract is devoid of boswellic acids;
b. a composition comprising an effective amount of an alcohol extract of *Boswellia frereana*, wherein said extract comprises epi-lupeol or a salt thereof, and wherein the extract is devoid of boswellic acids; or
c. a combination therapeutic comprising:
   i.) an effective amount of an alcohol extract of *Boswellia frereana*, wherein said extract comprises epi-lupeol or a salt thereof, and wherein the extract is devoid of boswellic acids; and
   ii.) an additional therapeutic.

7. The method of claim 6, wherein said extract comprises one or more of the following: β-amyrin, α-amyrin, α-phellandrene dimers, α-thujene, and α-phellandrene, and isomers or salts thereof.

8. The method of claim 6, wherein said extract comprises one or more of the following: β-amyrin, α-phellandrene dimers, and isomers or salts thereof.

9. The method of claim 6, wherein said extract is a methanol extract.

10. The method of claim 6, wherein said extract is an ethanol extract.

\* \* \* \* \*

SEQUENCE LISTING

```
<160> NUMBER OF SEQ ID NOS: 6

<210> SEQ ID NO 1
<211> LENGTH: 20
<212> TYPE: DNA
<213> ORGANISM: artificial
<220> FEATURE:
<223> OTHER INFORMATION: quantitative PCR assay primers

<400> SEQUENCE: 1
tgttcagctg tgccttcaac                                              20

<210> SEQ ID NO 2
<211> LENGTH: 20
<212> TYPE: DNA
<213> ORGANISM: artificial
<220> FEATURE:
<223> OTHER INFORMATION: quantitative PCR assay primer

<400> SEQUENCE: 2
aaagcgcaga actgagggta                                              20

<210> SEQ ID NO 3
<211> LENGTH: 20
<212> TYPE: DNA
<213> ORGANISM: artificial
<220> FEATURE:
<223> OTHER INFORMATION: quantitative PCR assay primer

<400> SEQUENCE: 3
ggacgctcag agacatggag                                              20

<210> SEQ ID NO 4
<211> LENGTH: 21
<212> TYPE: DNA
<213> ORGANISM: artificial
<220> FEATURE:
<223> OTHER INFORMATION: quantitative PCR assay primer

<400> SEQUENCE: 4
tatgccacgg tgtgtaccat a                                            21

<210> SEQ ID NO 5
<211> LENGTH: 20
<212> TYPE: DNA
<213> ORGANISM: artificial
<220> FEATURE:
<223> OTHER INFORMATION: quantitative PCR assay primer

<400> SEQUENCE: 5
tagcacgcac gacatctttc                                              20
```

```
<210> SEQ ID NO 6
<211> LENGTH: 20
<212> TYPE: DNA
<213> ORGANISM: artificial
<220> FEATURE:
<223> OTHER INFORMATION: quantitative PCR assay primer

<400> SEQUENCE: 6
gaaggtcacg tagcccacat                                        20
```